US009204835B2

(12) United States Patent
Parsey et al.

(10) Patent No.: US 9,204,835 B2
(45) Date of Patent: Dec. 8, 2015

(54) VOXEL-BASED METHODS FOR ASSESSING SUBJECTS USING POSITRON EMISSION TOMOGRAPHY

(75) Inventors: Ramin Parsey, Mountain Lakes, NJ (US); Arthur Mikhno, New City, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 791 days.

(21) Appl. No.: 12/917,113

(22) Filed: Nov. 1, 2010

(65) Prior Publication Data
US 2011/0160543 A1 Jun. 30, 2011

Related U.S. Application Data

(63) Continuation-in-part of application No. PCT/US2009/045537, filed on May 28, 2009.

(60) Provisional application No. 61/056,780, filed on May 28, 2008.

(51) Int. Cl.
| | | |
|---|---|---|
| A61B 5/05 | (2006.01) | |
| A61B 5/16 | (2006.01) | |
| A61B 5/055 | (2006.01) | |
| A61B 6/03 | (2006.01) | |
| A61B 6/00 | (2006.01) | |
| G01R 33/00 | (2006.01) | |
| G01R 33/10 | (2006.01) | |
| G06T 7/00 | (2006.01) | |
| G06T 7/40 | (2006.01) | |

(52) U.S. Cl.
CPC . *A61B 5/16* (2013.01); *A61B 5/055* (2013.01); *A61B 6/037* (2013.01); *A61B 6/501* (2013.01); *A61B 6/5247* (2013.01); *A61B 6/56* (2013.01); *A61B 6/563* (2013.01); *G01R 33/0023* (2013.01); *G01R 33/10* (2013.01); *G06T 7/0012* (2013.01); *G06T 7/401* (2013.01); *G06T 2207/10088* (2013.01); *G06T 2207/10104* (2013.01); *G06T 2207/20128* (2013.01); *G06T 2207/30016* (2013.01)

(58) Field of Classification Search
None
See application file for complete search history.

(56) References Cited

U.S. PATENT DOCUMENTS

| | | | | |
|---|---|---|---|---|
| 5,590,215 | A | * 12/1996 | Allen | 382/128 |
| 5,603,322 | A | * 2/1997 | Jesmanowicz et al. | 600/410 |
| 6,001,331 | A | 12/1999 | Caprathe et al. | |
| 6,133,259 | A | 10/2000 | Klunk et al. | |
| 6,168,776 | B1 | 1/2001 | Klunk et al. | |
| 6,249,594 | B1 * | 6/2001 | Hibbard | 382/128 |

(Continued)

OTHER PUBLICATIONS

Chetelat et al., Direct voxel-based comparison between grey matter hypometabolism and atrophy in Alzheimer's disease, Brain (2008), 131, 60-71.*

(Continued)

*Primary Examiner* — Nicholas Evoy
(74) *Attorney, Agent, or Firm* — Wilmer Cutler Pickering Hale and Dorr LLP

(57) ABSTRACT

The subject matter disclosed herein relates to methods for diagnosing a neurological disorder in a subject. In certain aspects, the methods described herein involve determining one or more critical areas in the brain from PET data where two groups differ and measuring PET signal within determined critical areas in a new subject in order to assign risk or diagnosis.

51 Claims, 10 Drawing Sheets

(56) References Cited

U.S. PATENT DOCUMENTS

| | | | |
|---|---|---|---|
| 6,430,430 B1* | 8/2002 | Gosche | 600/410 |
| 6,611,630 B1* | 8/2003 | Miller et al. | 382/293 |
| 6,696,039 B2 | 2/2004 | Kung et al. | |
| 6,950,544 B2* | 9/2005 | Ashton | 382/131 |
| 7,069,068 B1* | 6/2006 | Ostergaard | 600/420 |
| 7,092,748 B2* | 8/2006 | Valdes Sosa et al. | 600/407 |
| 7,127,095 B2* | 10/2006 | El Fakhri et al. | 382/128 |
| 7,251,374 B2* | 7/2007 | Niemeyer | 382/240 |
| 7,251,523 B2* | 7/2007 | Kojima et al. | 600/427 |
| 7,558,417 B2* | 7/2009 | Knoplioch et al. | 382/131 |
| 7,672,790 B2* | 3/2010 | McGraw et al. | 702/19 |
| 7,751,602 B2* | 7/2010 | Collins et al. | 382/128 |
| 7,787,671 B2* | 8/2010 | De Leon et al. | 382/128 |
| 7,889,895 B2* | 2/2011 | Nowinski et al. | 382/128 |
| 7,961,922 B2* | 6/2011 | Spence et al. | 382/128 |
| 8,059,879 B2* | 11/2011 | Tsukimoto | 382/131 |
| 8,090,429 B2* | 1/2012 | Vija et al. | 600/427 |
| 8,160,314 B2* | 4/2012 | Ramamurthy et al. | 382/128 |
| 8,280,482 B2* | 10/2012 | Rusinek et al. | 600/407 |
| 8,423,118 B2* | 4/2013 | Wenzel et al. | 600/407 |
| 8,463,552 B1* | 6/2013 | Black et al. | 702/19 |
| 8,600,135 B2* | 12/2013 | Patriarche et al. | 382/128 |
| 8,908,948 B2* | 12/2014 | Fan et al. | 382/128 |
| 9,053,534 B2* | 6/2015 | Ross et al. | 1/1 |
| 2004/0062345 A1* | 4/2004 | Kojima et al. | 378/19 |
| 2004/0161138 A1* | 8/2004 | Ashton | 382/128 |
| 2004/0210124 A1* | 10/2004 | Nowinski et al. | 600/407 |
| 2005/0035296 A1* | 2/2005 | Kojima et al. | 250/363.03 |
| 2005/0110490 A1* | 5/2005 | Zhao et al. | 324/311 |
| 2005/0119547 A1* | 6/2005 | Shastri et al. | 600/407 |
| 2005/0154290 A1* | 7/2005 | Langleben | 600/410 |
| 2005/0283054 A1* | 12/2005 | Reiman | 600/300 |
| 2006/0018825 A1 | 1/2006 | Kudo et al. | |
| 2006/0025673 A1* | 2/2006 | De Leon et al. | 600/410 |
| 2006/0036152 A1* | 2/2006 | Kozel | 600/410 |
| 2006/0083415 A1* | 4/2006 | El Fakhri et al. | 382/128 |
| 2006/0084858 A1* | 4/2006 | Marks | 600/407 |
| 2006/0104494 A1* | 5/2006 | Collins et al. | 382/128 |
| 2006/0115137 A1* | 6/2006 | Knoplioch et al. | 382/131 |
| 2007/0014463 A1* | 1/2007 | El Fakhri et al. | 382/128 |
| 2007/0019846 A1* | 1/2007 | Bullitt et al. | 382/128 |
| 2007/0088211 A1* | 4/2007 | Cheng et al. | 600/410 |
| 2007/0191704 A1* | 8/2007 | DeCharms | 600/411 |
| 2007/0282189 A1* | 12/2007 | Dan et al. | 600/407 |
| 2008/0101665 A1* | 5/2008 | Collins et al. | 382/128 |
| 2008/0247622 A1* | 10/2008 | Aylward et al. | 382/131 |
| 2009/0028403 A1* | 1/2009 | Bar-Aviv et al. | 382/128 |
| 2009/0279762 A1* | 11/2009 | Tsukimoto | 382/131 |
| 2010/0174174 A1* | 7/2010 | Kabasawa | 600/419 |
| 2010/0249573 A1* | 9/2010 | Marks | 600/411 |
| 2010/0260396 A1* | 10/2010 | Brandt et al. | 382/131 |
| 2011/0160543 A1* | 6/2011 | Parsey et al. | 600/300 |
| 2011/0301431 A1* | 12/2011 | Greicius et al. | 600/300 |
| 2013/0223714 A1* | 8/2013 | Lipton et al. | 382/131 |
| 2013/0259346 A1* | 10/2013 | El-Baz et al. | 382/131 |
| 2013/0266201 A1* | 10/2013 | Pautot, Fabrice | 382/131 |
| 2014/0336503 A1* | 11/2014 | Kilbourn et al. | 600/425 |

OTHER PUBLICATIONS

Kanda et al., Comparison of grey matter and metabolic reductions in frontotemporal dementia using FDG-PET and voxel-based morphometric MR studies, Eur J Nucl Med Mol Imaging (2008) 35:2227-2234.*

Kerrouche et al., 18FDG PET in vascular dementia: differentiation from Alzheimer's disease using voxel-based multivariate analysis, Journal of Cerebral Blood Floow & Metabolism (2006) 26, 1213-1221.*

Matsuda, Role of Neuroimaging in Alzheimer's Disease, with Emphasis on Brain Perfusion SPECT, J Nucl Med 2007; 48:1289-1300.*

Matsunari et al, Comparison of 18F-FDG PET and Optimized Voxel-Based Morphometry for Detection of Alzheimer's Disease: Aging Effect on Diagnostic Performance, J Nucl Med 2007; 48:1961-1970.*

Mevel et al., Detecting hippocampal hypometabolism in Mild Cognitive Impairment using automatic voxel-based approaches, NeuroImage 37 (2007) 18-25.*

Mikhno et al., Voxel Based Analysis of 11C-PIB Scans for Diagnosing Alzheimer's Disease, J Nucl Med 2008; 49:1262-1269.*

Mosconi et al., 18F-FDG PET Database of Longitudinally Confirmed Healthy Elderly Individuals Improves Detection of Mild Cognitive Impairment and Alzheimer's Disease, J Nucl Med 2007; 48:1129-1134.*

Mosconi et al., Multicenter Standardized 18F-FDG PET Diagnosis of Mild Cognitive Impairment, Alzheimer's Disease, and Other Dementias, J Nucl Med 2008; 49:390-398.*

Truchot et al., A distinct [18]MPPF PET profile in amnestic mild cognitive impairment compared to mild Alzheimer's disease, NeuroImage 40 (2008) 1251-1256.*

Zahn et al., Mapping of temporal and parietal cortex in progressive nonfluent aphasia and Alzheimer's disease using chemical shift imaging, voxel-based morphometry and positron emission tomography, Psychiatry Research: Neuroimaging 140 (2005) 115-131.*

Ziolko et al., Evaluation of voxel-based methods for the statistical analysis of PIB PET amyloid imaging studies in AlzheimerTs disease, NeuroImage 33 (2006) 94-102.*

Ashburner J, Friston K J. Nonlinear spatial normalization using basis functions. Hum Brain Mapp. 1999; 7 (4):254-266.

Ashburner J, Friston K J. Unified segmentation. Neuroimage. Jul. 1 2005; 26 (3):839-851.

Boellaard et al., Effects of Noise, Image Resolution, and ROI Definition on the Accuracy of Standard Uptake Values: A Simulation StudyJ Nucl Med 2004; 45: 1519-1527.

Chetelat G, Landeau B, Eustache F, et al. Using voxel-based morphometry to map the structural changes associated with rapid conversion in MCI: a longitudinal MRI study. Neuroimage. Oct. 1, 2005; 27 (4):934-946.

Foundas A L, Eure K F, Seltzer B. Conventional MRI volumetric measures of parietal and insular cortex in Alzheimer's disease. Frog Neuropsychopharmacol Biol Psychiatry. Oct. 1996; 20 (7):1131-1144.

Gunn et al.,; Positron Emission Tomography Compartmnetal Models J Cereb Blood Flow Metab. 2001; 21: 635-652.

Gunn et al., Parametric Imaging of Ligand-Receptor Binding in PET Using a Simplified Reference Region Model NeuroImage 1997; 6:279-287.

Hoffman E J, Huang S C, Phelps M E. Quantitation in positron emission computed tomography: 1. Effect of object size. J Comput Assist Tomogr. Jun. 1979; 3 (3):299-308.

Huang, Anatomy of SUV; Nucl Med Biol 2000; 27: 643-646.

Innis et al., Consensus nomenclature for in vivo imaging of reversibly binding radioligandsJ Cereb Blood Flow; Metab. 2007; 27(9): 1533-1539.

Jenkinson M, Smith S. A global optimisation method for robust affine registration of brain images. Med Image Anal. Jun. 2001; 5 (2):143-156.

Joachim C L, Morris J H, Selkoe D J. Diffuse senile plaques occur commonly in the cerebellum in Alzheimer's disease. Am J Pathol. Aug. 1989; 135 (2):309-319.

Kanetaka H, Matsuda H, Asada T, et al. Effects of partial volume correction on discrimination between very early Alzheimer's dementia and controls using brain perfusion SPECT. Eur J Nucl Med Mol Imaging. Jul. 2004; 31 (7):975-980.

Kemppainen N M, Aalto S, Wilson I A, et al. PET amyloid ligand [.sup.11C]PIB uptake is increased in mild cognitive impairment. Neurology. May 8, 2007; 68 (19):1603-1606.

Kemppainen N M, Aalto S, Wilson I A, et al. Voxel-based analysis of PET amyloid ligand [.sup.11C]PIB uptake in Alzheimer disease. Nurology. Nov. 14, 2006; 67 (9):1575-1580.

Kimura Y, Naganawa M, Shidahara M, Ikoma Y, Watabe H. PET kinetic analysis—pitfalls and a solution for the Logan plot. Ann Nucl Med. Jan. 2007; 21 (1):1-8.

(56) References Cited

OTHER PUBLICATIONS

Klunk W E, Engler H, Nordberg A, et al. Imaging brain amyloid in Alzheimer's disease with Pittsburgh Compound-B. Ann Neurol. Mar. 2004; 55 (3):306-319.

Kudo et al. 2-(2[2-Dimethylaminothiazol-5-yl]Ethenyl)-6-(2-[Fluoro]Ethoxy)Benzoxazole: A Novel PET Agent for In Vivo Detection of Dense Amyloid Plaques in Alzheimer's Disease PatientsJ. Nucl. Med. 2007; 553-561.

Lammertsma and Hume, Simplified Reference Tissue Model for PET Receptor Studies; NeuroImage 1996; 4:153-158.

Lammertsma, Radio ligand studies: imaging and quantitative analysis; Eur Neuropsychopharmacol. 2002; 12: 513-516.

Logan J, Fowler J S, Volkow N D, Ding Y S, Wang G J, Alexoff D L. A strategy for removing the bias in the graphical analysis method. J Cereb Blood Flow Metab. Mar. 2001; 21 (3):307-320.

Logan J, Fowler J S, Volkow N D, Wang G J, Ding Y S, Alexoff D L. Distribution volume ratios without blood sampling from graphical analysis of PET data. J Cereb Blood Flow Metab. Sep. 1996; 16 (5):834-840.

Lopresti B J, Klunk W E, Mathis C A, et al. Simplified quantification of Pittsburgh Compound B amyloid imaging Pet studies: a comparative analysis. J Nucl Med. Dec. 2005; 46 (12): 1959-1972.

Mawlawi O, Martinez D, Slifstein M, et al. Imaging human mesolimbic dopamine transmission with positron emission tomography: I. Accuracy and precision of D(2) receptor parameter measurements in ventral striatum. J Cereb Blood Flow Metab. Sep. 2001; 21 (9):1034-1057.

Mazziotta J C, Toga A W, Evans A, Fox P, Lancaster J. A probabilistic atlas of the human brain: theory and rationale for its development. The International Consortium for Brain Mapping (ICBM). Neuroimage. Jun. 1995; 2 (2):89-101.

Mazziotta J, Toga A, Evans A, et al. A probabilistic atlas and reference system for the human brain: International Consortium for Brain Mapping (ICBM). Philos Trans R Soc Lond B Biol Sci. Aug. 29 2001; 356 (1412):1293-1322.

McKhann G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. Neurology. Jul. 1984; 34 (7):939-944.

Meltzer C C, Kinahan P E, Greer P J, et al. Comparative evaluation of MR-based partial-volume correction schemes for PET. J Nucl Med. Dec. 1999; 40 (12):2053-2065.

Meltzer C C, Zubieta J K, Brandt J, Tune L E, Mayberg H S, Frost J J. Regional hypometabolism in Alzheimer's disease as measured by positron emission tomography after correction for effects of partial volume averaging. Neurology. Aug. 1996; 47 (2):454 461.

Miller et al., Applications of Positron Emission Tomography in Neuropsychiatric Pharmaceutical Drug Development; Current Radiopharmaceuticals, 2008, 1, 12-16.

Minino A M, Heron M P, Murphy S L, Kochanek K D. Deaths: final data for 2004. Natl Vital Stat Rep. Aug. 21 2007; 55 (19):1-120.

Mintun et al. A Quantitative Model for the In Vivo Assessment of Drug Binding Sites with Positron Emission Tomography; Ann Neurol. 1984; 15: 217-227.

Mintun M A, Larossa G N, Sheline Y I, et al. [.sup.11C]PIB in a nondemented population: potential antecedent marker of Alzheimer disease. Neurology. Aug. 8 2006; 67 (3):446-452.

Mosconi L, Tsui W H, De Santi S, et al. Reduced hippocampal metabolism in MCI and AD: automated FDG-PET image analysis. Neurology. Jun. 14 2005; 64 (11):1860-1867.

Muller-Gartner H W, Links J M, Prince J L, et al. Measurement of radiotracer concentration in brain gray matter using positron emission tomography: MRI-based correction for partial volume effects. J Cereb Blood Flow Metab. Jul. 1992; 12 (4):571-583.

Ng S, Villemagne V L, Berlangieri S, et al. Visual assessment versus quantitative assessment of 11C-PIB PET and 18F-FDG PET for detection of Alzheimer's disease. J Nucl Med. Apr. 2007; 48 (4):547-552.

Okamura et al. Styrylbenzoxazole Derivatives for In Vivo Imaging of Amyloid Plaques in the BrainJ. Neurosci. 2004; 24 (10), 2535-2541.

Parsey R V, Sokol L O, Belanger M J, et al. Amyloid plaque imaging agent [C-11]-6-OH-BTA-1: biodistribution and radiation dosimetry in baboon. Nucl Med Commun. Oct. 2005; 26 (10):875-880.

Price J C, Klunk W E, Lopresti B J, et al. Kinetic modeling of amyloid binding in humans using PET imaging and Pittsburgh Compound-B. J Cereb Blood Flow Metab. Nov. 2005; 25 (11): 1528-1547.

Rousset O G, Ma Y, Evans A C. Correction for partial volume effects in PET: principle and validation. J Nucl Med. May 1998; 39 (5):904-911.

Rowe C C, Ng S, Ackermann U, et al. Imaging beta-amyloid burden in aging and dementia. Neurology. May 15, 2007; 68 (20):1718-1725.

Royall D R, Gao J H, Kellogg D L, Jr. Insular Alzheimer's disease pathology as a cause of "age-related" autonomic dysfunction and mortality in the non-demented elderly. Med Hypotheses. 2006; 67 (4):747-758.

Rusjan P, Mamo D, Ginovart N, et al. An automated method for the extraction of regional data from PET images. Psychiatry Res. Jun. 30 2006; 147 (1):79-89.

Schmidt and Turkheimer, Kinetic modeling in positron emission tomography Q J Nucl Med. 2002; 46:70-85.

Slifstein et al., Models and methods for derivation of in vivo neuroreceptor parameters with PET and SPECT reversible radiotracers; Nucl. Med. Biol. 2001; 28: 595-608.

Smith S M. Fast robust automated brain extraction. Hum Brain Mapp. Nov. 2002; 17 (3):143-155.

Thal D R, Rub U, Orantes M, Braak H. Phases of A beta-deposition in the human brain and its relevance for the development of AD. Neurology. Jun. 25 2002; 58 (12):1791-1800.

The Turku PET Center Image Analysis Guide available at http://www.turkupetcentre.fi/index.php?option=com_content&view=article&id=24&Itemid=69&lang=en; 50 pages.

Thie, Understanding the Standardized Uptake Value, Its Methods, and Implications for Usage; J Nucl Med 2004; 45: 1431-1434.

Watson C C N D, Casey M E. A single scatter simulation technique for scatter correction in 3D PET. Dordrecht. 1996; 255-268.

Zamrini E, De Santi S, Tolar M. Imaging is superior to cognitive testing for early diagnosis of Alzheimer's disease. Neurobiol Aging. May-Jun. 2004; 25 (5):685-691.

Zhou Y, Resnick S M, Ye W, et al. Using a reference tissue model with spatial constraint to quantify [.sup.11C] Pittsburgh compound B PET for early diagnosis of Alzheimer's disease. Neuroimage. Jun. 2007; 36 (2):298-312.

Ziolko S K, Weissfeld L A, Klunk W E, et al. Evaluation of voxel-based methods for the statistical analysis of PIB PET amyloid imaging studies in Alzheimer's disease. Neuroimage. Oct. 15 2006; 33 (1):94-102.

\* cited by examiner

VOXEL-BASED METHODS FOR ASSESSING SUBJECTS USING POSITRON EMISSION TOMOGRAPHY

This application is a continuation in part of International Patent Application No. PCT/US2009/045537, filed May 28, 2009 and claims the benefit of, and priority to, U.S. provisional patent application Ser. No. 61/056,780 filed May 28, 2008, the disclosures of all of which are hereby incorporated by reference in its entirety for all purposes.

This invention was made with government support under R01AG017761 awarded by the National Institutes of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the subject matter disclosed herein.

BACKGROUND

Alzheimer's disease (AD) is characterized by memory loss, cognitive impairment, and behavioral changes. More than 15 million people suffer from AD worldwide and this disease is the $7^{th}$ leading cause of death in the United States (1). Many neurological disorders can be attributed to deregulated protein levels in the brain. AD pathology is characterized by extra-cellular amyloid beta (Aβ) neuritic plaques and intracellular neurofibrillary tangles. Aβ plaques are toxic and progressively accumulate in the brain throughout the duration of the disease, resulting in neuronal loss and cortical atrophy. Excessive Aβ accumulation eventually involves much of the neocortex, hippocampus and many subcortical structures.

Diagnosis of AD can be performed by clinical examination using the National Institute of Neurological and Communicative Diseases and Stroke/Alzheimer's Disease and Related Disorders Association (NINCDS-ADRDA) criteria. This method ranges from 76 to 98% sensitivity and 61 to 84% specificity (2). The wide range partly depends on the stage of the disease at the time of examination and clinical skill. Clinical diagnosis is more accurate in later stages of the disease. Early stage AD is more difficult to diagnose. Clinical symptoms appear after significant deposition of Aβ has already occurred (3). The ability to detect early stage AD in a specific and sensitive manner prior to the occurrence of significant impairment, and the advent of new therapeutic agents that work by arresting Aβ accumulation or depletion of Aβ levels in the brain, are important to early treatment and inhibition of disease progression.

Positron Emission Tomography (PET) can measure a variety of physical parameters, including, but not limited to, absolute blood flow, glucose metabolism, and the level of a particular molecule in the brain. PET scans can also be used to distinguish patients based on diagnosis, assign risk or adverse events (e.g. suicide), or to predict treatment response. There is a need to develop PET-based methods for diagnosing and making treatment decisions in subjects having, or at risk of having a neurological disorder, such as AD. This subject matter disclosed herein addresses this need.

SUMMARY

In one aspect, the methods described herein relate to a computer-implemented method for diagnosing or determining risk of a neurological disorder in a subject, the method comprising: (a) generating primary brain scan image voxel data of radioligand distribution in a brain of at least one individual in a control group and at least one individual in a reference group, (b) generating secondary brain scan image data for the individuals in the control and reference groups, wherein the secondary scan brain image data is generated using a different type of brain scan than the primary brain scan image data, (c) generating a probability-corrected time-activity curve data for each voxel in the primary brain scan image of the at least one individual in the control and reference group, (d) processing the probability-corrected time-activity curve data of the at least one individual in the control and reference group to generate a voxel binding outcome mdata of the at least one individual in the control and reference group, (e) transforming the voxel binding outcome map data of the at least one individual in the control and reference group into a normalized space to generate a normalized voxel binding outcome map data of the at least one individual in the control and reference group, (f) processing the normalized voxel binding outcome map data of the at least one individual in the control and reference group using statistical analysis to identify one or more voxels of interest (VOI) in the normalized voxel binding outcome map data to generate a VOI map data for differentiating of the at least one individual in the control and reference group, and (g) applying the VOI map data to a voxel binding outcome map data of a test subject to generate a mean cortical binding value to diagnose or determine risk of a neurological disorder in the subject.

In one embodiment, the transforming the voxel binding outcome map data of the at least one individual in the control and reference group into a normalized space to generate a normalized voxel binding outcome map data of the at least one individual in the control and reference group comprises transforming the voxel binding outcome map data of the at least one individual in the control and reference group into a secondary scan space to generate a secondary space voxel binding outcome map data of the at least one individual in the control and reference group. In one embodiment, the transforming the voxel binding outcome map data of the at least one individual in the control and reference group into a normalized space comprises co-registration.

In one embodiment, applying the VOI map data to a voxel binding outcome map data of a test subject to generate a mean cortical binding value to diagnose or determine risk of a neurological disorder in the subject comprises: (i) inverse transforming the VOI map data identified in step (f), into a primary brain scan image of the test subject to generate a voxel of interest (VOI) mask for the test subject, (ii) multiplying the voxel of interest (VOI) mask for the subject by probabilistic brain region (BRP) map data for the subject to generate a brain region VOI mask for the subject, (iii) multiplying a secondary space voxel binding outcome map data of the subject by the brain region VOI mask for the subject to generate cortical binding map data for the subject, and (iv) summing the cortical binding map data of the subject and then dividing it by the sum of the brain region VOI mask to generate a mean cortical binding value. In one embodiment, the method further comprises a step of processing the secondary brain scan image data of the subject by partial volume correction analysis.

In one embodiment, the inverse transforming is performed using parameters from an MRI to standard brain atlas registration.

In one embodiment, the generating a probability-corrected time-activity curve data for each voxel in the primary brain scan image of the at least one individual in the control and reference group in step (c) comprises (i) processing the secondary brain scan image data of the at least one individual in the control and reference group to generate a binary brain region mask and probabilistic brain region (BRP) map data for each individual, and (ii) processing the probabilistic brain region (BRP) map data and the primary brain scan image data of the at least one individual in the control and reference group onto the binary brain region mask of the individual to generate the a probability-corrected time-activity curve data for each voxel in the primary brain scan image of the at least one individual in the control and reference group.

In one embodiment, the normalized voxel binding outcome map data of the at least one individual in the control and reference group is generated by transformation of secondary space voxel binding outcome map data of the individual into a standard brain atlas.

In one embodiment, the standard brain atlas is a Talairach brain atlas or a Montreal Neurological Institute (MNI) brain atlas. In another embodiment, the standard brain atlas is a specific brain atlas created for a particular neurological disorder. In yet another embodiment, the standard brain atlas is a custom brain atlas.

In one embodiment, the processing the normalized voxel binding outcome map data of the at least one individual in the control and reference group using statistical analysis to identify one or more voxels of interest (VOI) in the normalized voxel binding outcome map data to generate a VOI map data for differentiating of the at least one individual in the control and reference group comprises: (i) generating a binary voxel image mask of the at least one individual in the control and reference group by statistical parametric mapping analysis, (ii) inverse transforming the binary voxel image mask of the at least one individual in the control and reference group into a secondary space voxel binding outcome map data of the individual to generate a voxel of interest (VOI) mask, (iii) multiplying the VOI mask of the at least one individual in the control and reference group by the individual's probabilistic brain region (BRP) map data and secondary space voxel binding outcome map data to generate cortical binding map data for the individual, (iv) dividing the sum of the cortical binding map of the at least one individual in the control and reference group and the reference group by the mean of the probabilistic brain region (BRP) map data of the individual to generate a mean cortical binding outcome value for the statistical parametric mapping analysis applied in step (i), (v) performing statistical analysis between the mean cortical binding outcome values of the at least one individual in the control and reference group to generate a map assigning a probability value to each voxel, and (vi) identifying a scoring threshold providing maximal separation of mean cortical binding outcome values between the at least one individual in the control and reference group, wherein the VOI corresponding to the scoring threshold providing maximal separation of mean cortical binding outcome between individuals from the control group and individuals from the reference group is a VOI map data suitable for differentiating individuals in the reference group from individuals in the control group. In one embodiment, the statistical analysis in step (v) is a Student's t test. In one embodiment, the generating of the binary voxel image mask in step (i) comprises applying one or more threshold values are to the normalized voxel binding outcome map data such that, for each threshold, data in the voxel binding outcome map data equal to or exceeding the threshold value are retained in the binary voxel image mask and data in the voxel binding outcome map data less than the threshold value are not retained in the binary voxel image mask. In one embodiment, the one or more threshold values are greater or equal to a value of 50% mean cortical binding outcome in each voxel in the normalized voxel binding outcome map data. In one embodiment, the one or more threshold values are greater or equal to a value of 90% mean cortical binding outcome in each voxel in the normalized voxel binding outcome map data. In one embodiment, the one or more threshold values are greater or equal to a value of 99% mean cortical binding outcome in each voxel in the normalized voxel binding outcome map data.

In one embodiment, the secondary space voxel binding outcome map data is generated using a different type of brain scan than the primary brain scan image data used in step (a).

In one embodiment, the primary brain scan image data is generated using an arterial input function as a reference.

In another embodiment, the secondary brain scan image data is from the cerebellum of the individual.

In still another embodiment, the secondary brain scan image data is from one or more regions of the cerebellum.

In yet another embodiment, the secondary brain scan image data is from one or more regions of having reduced radioligand binding.

In one embodiment, the processing in step (d) comprises Logan graphical analysis. In one embodiment, a brain region probability corrected time activity curve of the cerebellum is used as a reference region.

In one embodiment, the brain region is gray matter. In another embodiment, the brain region is white matter. In yet another embodiment, the brain region is cerebrospinal fluid. In still another embodiment, the brain region is a brain region comprising one of more voxels in step (c).

In one embodiment, the normalized space voxel binding outcome map data is processed by partial volume correction before step (g).

In one embodiment, the partial volume correction analysis comprises a three-compartment method. In another embodiment, the partial volume correction analysis comprises a two-compartment method.

In one embodiment, the transforming the voxel binding outcome map data of the at least one individual in the control and reference group into a normalized space to generate a normalized voxel binding outcome map data of the at least one individual in the control and reference group is performed using an algorithm selected from the group consisting of any of Statistical Parametric Mapping (SPM), Simple Affine (AFF) methodology, the Fifth Order Polynomial Warp (WRP) methodology, and the Full Multi Grid (FMG) methodology. In another embodiment, the transforming the voxel binding outcome map data of the at least one individual in the control and reference group into a normalized space to generate a normalized voxel binding outcome map data of the at least one individual in the control and reference group is performed using an algorithm is selected from the group consisting of AIR, ANIMAL, ART, Diffeomorphic Demons, FNIRT, IRTK, JRD-fluid, ROMEO, SICLE, SyN and FLIRT.

In one embodiment, individuals in the control group and the reference group are separated into groups according to the presence or absence of a neurological disorder.

In one embodiment, the neurological disorder is Alzheimer's disease.

In another embodiment, the neurological disorder is selected from the group consisting of mild cognitive impairment, Dementia, Alzheimer's disease, multi-infarct dementia, Pick's disease, Creutzfeldt-Jakob disease, Huntington's disease, Parkinson's disease, AIDS dementia complex, frontotemporal dementia, sundowning, wandering, delirium, post-concussion syndrome, organic brain syndrome, intoxication/drug overdose, physical dependence, substance dependence, rebound effect, double rebound, withdrawal, psychosis (e.g. schizoaffective disorder, schizophreniform disorder, brief reactive psychosis), schizophrenia (e.g. disorganized schizophrenia, delusional disorder, folie à deux), mood disorders, mania, bipolar disorders (e.g. bipolar I, bipolar II, cyclothymia, bipolar NOS), depression (e.g. major depressive disorder, dysthymia, seasonal affective disorder, atypical depression, melancholic depression), anxiety disorders, phobias, panic disorder/panic attack, generalized anxiety disorder, OCD, stress disorders (e.g. acute stress reaction, PTSD), adjustment disorder with depressed mood, somatoform disorders, somatization disorder, body dysmorphic disorder, hypochondriasis, nosophobia, Da Costa's syndrome, psychalgia, conversion disorders (e.g. Ganser syndrome, Globus pharyngis), neurasthenia, mass psychogenic illness, dissociative disorders, dissociative identity disorder, psychogenic amnesia, fugue state, depersonalization disorder, eating disorders, anorexia nervosa, bulimia nervosa, rumination syndrome, NOS, nonorganic sleep disorders, nonorganic hypersomnia, nonorganic insomnia, parasomnia disorders (e.g. REM behavior disorder, night terror, nightmare), sexual dysfunction, sexual desire disorders (e.g. hypoactive sexual desire disorder, hypersexuality), sexual arousal (e.g. female sexual arousal disorder), erectile dysfunction, orgasm disorders (e.g. anorgasmia, premature ejaculation), postpartum depression, postnatal psychosis, adult personality and behavior disorders, sexual maturation disorder, ego-dystonic sexual orientation, sexual relationship disorder, paraphilia disorders (e.g. voyeurism, fetishism), personality disorder, impulse control disorder (e.g. kleptomania, Trichotillomania, Pyromania), body-focused repetitive behavior, factitious disorders (e.g. Munchausen syndrome), mental retardation, phychological development disorders, ADHD, conduct disorders (e.g. ODD), emotional disorders (e.g. Separation anxiety disorder), social functioning disorders (e.g. selective mutism, RAD, DAD), tic disorders (e.g. Tourette syndrome), speech disorders (e.g. stuttering, cluttering), movement disorders (e.g. stereotypic movement disorder), catatonia, false pregnancy, intermittent explosive disorder, psychomotor agitation, sexual addiction, stereotypy, psychogenic non-epileptic seizures, Klüver-Bucy syndrome, Emil Kraepelin mood disorder, Karl Leonhard mood disorder, John Cade mood disorder, Mogens Schou mood disorder, Frederick K. Goodwin mood disorder, Kay Redfield Jamison mood disorder, hallucination, delusion, emotional dysregulation disorders (e.g. anhedonia, dysphoria, suicidal ideation), sleep disorders (e.g. hypersomnia, insomnia), psychosis, and racing thoughts.

In another embodiment, the neurological disorder is a reduced responsiveness to a compound administered to the subject as compared to a control subject.

In yet another embodiment, the neurological disorder is an increased responsiveness to a compound administered to the subject as compared to a control subject.

In one embodiment, the compound is a selective serotonin reuptake inhibitor. In another embodiment, the compound is selected from the group consisting of an analgesic, an anesthetic, an anorectic, an anti-adhd agent, an antiaddictive, an anticonvulsant, an antidementia agent, an antidepressant, an antimigraine agent, an antiparkinson's agent, an antipsychotic, an anxiolytic, a depressant, an entactogen, an entheogen, an euphoriant, a hallucinogen, hypnotics/sedative, a mood stabilizer, a neuroprotective, a nootropic, a neurotoxins, an orexigenic, a serenic, a stimulant, and a wakefulness-promoting agent.

In one embodiment, the method further comprises a step of administering the radioligand to the one or more individuals in the control group and to the one or more individuals in the reference group before generating primary brain scan image voxel data of radioligand distribution in a brain of at least one individual in a control group and at least one individual in a reference group.

In one embodiment, the radioligand is N-methyl-[11C]2-(4-methylaminophenyl)-6-hydroxybenzothiazole. In another embodiment, the radioligand is [11C]WAY-100635. In yet another embodiment, the radioligand is selected from the group consisting of [11C]-DTBZ, 11CFE-CIT, [18F]-dopa, [11C]-dopa, [18F]-CFT, [11C]-RTI-32, [18F]-FP-CIT, [11C]-methylphenidate, [123I]-β-CIT, [123I]-FP-CIT, [123I]-altropane, [99 mTc]-TRODAT-1, [11C]-dihydrotetrabenazine, [99mTc]-MHMPAO, [99 mTc]-ethylcystein dimer, [99 mTc]-DTPA, [99mTc]-glucoheptonate, [99mTc]-sestamibi, [99mTc]-tetrofosmin, [99mTc]-labelled sulphur colloid, H215O, [18F]-fluorodeoxyglucose, [13N]-ammonium, [15O]-butanol, 113Xe, 15O2, [11C]-CFT, [123I]-IPT, [11C]-SCH23390, [11C]-raclopride, [11C]-FLB456, [11C]-methylspiperone, [18F]-spiperone, [18F]-fluroethylspiperone, [76Br]-bromospiperone, [123I]-eppidepride, [123I]-iodobenzamide, [11C]-BATA, [18F]-2-fluorothoxydazoxan, [11C]-methyltryptophan, [11C]-DASB, [11C]-MDL100907, [18F]-altanserin, [18F]-serpeptone, [11C]-MP4A, [11C]-physostigmine, [18F]-fluoroethozybenzoessamicol, [11C]-vesamicol, [123I]-benzovesamicol, [11C]-tropanylbenylate, [11C]-NMPB, [18F]-FP-TZTP, [123I]-QNB, [11C]-MPA, [11C]-A-85380, [18F]-A-85380, [123I]-A-85380, [11C]-dothiepin, [11C]-carfentenil, [18F]-cyclofoxy, [11C]diprenorphine, [11C]-flumazenil, [11C]-RO15-4513, [11C]-PK11195, [18F]-PK11195, [123I]-PK11195, [18F]-SPARQ, [11C]-GR205171, [11C]-SCH 442416, [11C]-CNS 5161, [18F]-FDDNP, [11C]-SB13, [123I]-IMPY, and [11C]-carfentenil.

In one embodiment, the primary brain space image is generated using Positron Emission Tomography.

In one embodiment, the secondary brain space image is generated using Magnetic Resonance Imaging.

In one embodiment, the binding outcome is a specific-to-nonspecific equilibrium partition coefficient ($BP_{ND}$). In another embodiment, the binding outcome is a binding potential relative to plasma (BPP). In yet another embodiment, the binding outcome is a binding potential relative to free plasma concentration ($BP_F$). In still another embodiment, the binding outcome is standardized uptake value (SUV). In yet another embodiment, the binding outcome is determined by a standardization technique that generates a qualitative or quantitative measure of radioligand uptake or binding.

In one aspect, the methods described herein relate to a computer-implemented method for diagnosing or determining risk of a neurological disorder in a subject, the method comprising: (a) generating primary brain scan image data of radioligand distribution in a brain of at least one individual in a control group and at least one individual in a reference group, (b) generating secondary brain scan image data for the individuals in the control and reference groups, wherein the secondary scan brain image data is generated using a different type of brain scan than the primary brain scan image data, (c)

generating a probability-corrected time-activity curve data for each individual, (d) processing the probability-corrected time-activity curve data of the individuals in the control and reference groups to generate voxel mean cortical binding potential ($BP_{ND}$) map data for each individual, (e) transforming the voxel $BP_{ND}$ map data of the individuals in the control and reference groups into a secondary scan space to generate secondary space voxel $BP_{ND}$ map data for each individual, (f) transforming the secondary space voxel $BP_{ND}$ map data of the individuals in the control and reference groups onto a standardized space to generate normalized voxel $BP_{ND}$ map data for the individual, (g) processing the normalized voxel $BP_{ND}$ map data of individuals in the control group and the reference group using statistical analysis to identify one or more voxels of interest (VOI) in the normalized voxel $BP_{ND}$ map data to generate a VOI map data for differentiating individuals in the reference group from individuals in the control group, and (h) applying the VOI map data to a normalized voxel $BP_{ND}$ map data of a test subject to diagnose or determine risk of a neurological disorder in the subject.

In one embodiment, applying the VOI map data to a normalized voxel $BP_{ND}$ map data of a test subject to diagnose or determine risk of a neurological disorder in the subject comprises, inverse transforming the VOI identified in step (g), into the standardized space to generate a voxel of interest (VOI) mask for the subject, multiplying the voxel of interest (VOI) mask for the subject by probabilistic gray matter ($GM_p$) map data for the subject to generate a gray matter VOI mask for the subject, multiplying a secondary space voxel $BP_{ND}$ map data of the subject by the gray matter VOI mask for the subject to generate cortical binding map data for the subject, and summing the cortical binding map data of the subject and then dividing it by the sum of the gray matter VOI mask to generate a map of VOI radioligand accumulation.

In another embodiment applying the VOI map data to a normalized voxel $BP_{ND}$ map data of a test subject to diagnose or determine risk of a neurological disorder in the subject further comprises a step of processing the secondary space voxel $BP_{ND}$ map data of the subject by partial volume correction analysis.

In one embodiment, generating a probability-corrected time-activity curve data for each individual processing the secondary brain scan image data of the individuals in the control and reference groups to generate a binary gray matter mask and probabilistic gray matter ($GM_p$) map data for each individual, processing the $GM_p$ map data and the primary brain scan image data of the individuals in the control and reference groups onto the binary gray matter mask of the individual to generate the probability-corrected time-activity curve.

In still a further embodiment, the normalized voxel $BP_{ND}$ map data for the individual is generated by transformation of the secondary space voxel $BP_{ND}$ map data of the individual into a standard brain atlas.

In yet another embodiment, the normalized voxel $BP_{ND}$ map data is generated by transformation of the secondary space voxel $BP_{ND}$ map data of the subject into a standard brain atlas.

In one embodiment, the standard brain atlas is a Talairach brain atlas or a Montreal Neurological Institute (MNI) brain atlas. In another embodiment, the standard brain atlas is a specific brain atlas created for a particular neurological disorder.

In still another embodiment, inverse transforming the VOI identified in step (g), into the standardized space to generate a voxel of interest (VOI) mask for the subject is performed using parameters from an MRI to standard brain atlas registration.

In still a further embodiment, processing the normalized voxel $BP_{ND}$ map data of individuals in the control group and the reference group using statistical analysis to identify one or more voxels of interest (VOI) in the normalized voxel $BP_{ND}$ map data to generate a VOI map data for differentiating individuals in the reference group from individuals in the control group comprises (a) generating a binary voxel image mask of individuals from the control group and the reference group by statistical parametric mapping analysis, (b) inverse transforming the binary voxel image mask of individuals in the control group and the reference group into the secondary scan space of the individual to generate a voxel of interest (VOI) mask, (c) multiplying the VOI mask individuals in the control group and the reference group by the individual's GMp and secondary space voxel $BP_{ND}$ map data to generate cortical binding map data for the individual, (d) dividing the sum of the cortical binding map data individuals in the control group and the reference group by the mean of the GMp of the individual to generate a mean cortical $BP_{ND}$ value for thresholds applied in step (a), (e) performing statistical analysis between the mean cortical $BP_{ND}$ values of individuals in the control group and in the reference group to generate a map assigning a probability value to each voxel, and (f) identifying a scoring threshold providing maximal separation of mean cortical $BP_{ND}$ values between individuals from the control group and individuals from the reference group, wherein the VOI corresponding to the scoring threshold providing maximal separation of mean cortical $BP_{ND}$ between individuals from the control group and individuals from the reference group is a VOI map data suitable for differentiating individuals in the reference group from individuals in the control group.

In one embodiment, the statistical analysis performed between the mean cortical $BP_{ND}$ values of individuals in the control group and in the reference group to generate a map assigning a probability value to each voxel is a Student's t test.

In still a further embodiment, generating a binary voxel image mask of individuals from the control group and the reference group by statistical parametric mapping analysis comprises applying one or more threshold values are to the normalized voxel $BP_{ND}$ map data such that, for each threshold, data in the voxel $BP_{ND}$ map data equal to or exceeding the threshold value are retained in the binary voxel image mask and data in the voxel $BP_{ND}$ map data less than the threshold value are not retained in the binary voxel image mask.

In one embodiment, the one or more threshold values are greater or equal to a value of 50% mean cortical binding potential in each voxel in the normalized voxel $BP_{ND}$ map data. In another embodiment, the one or more threshold values are greater or equal to a value of 90% mean cortical binding potential in each voxel in the normalized voxel $BP_{ND}$ map data. In still a further embodiment, the one or more threshold values are greater or equal to a value of 99% mean cortical binding potential in each voxel in the normalized voxel $BP_{ND}$ map data.

In yet another embodiment, the primary brain scan image data is generated using an arterial input function as a reference.

In still another embodiment, the secondary brain scan image data is from the cerebellum of the individual.

In another embodiment, the secondary brain scan image data is from one or more regions of the cerebellum.

In yet another embodiment, the secondary brain scan image data is from one or more regions of having reduced radioligand binding.

In still another embodiment, the transforming of the voxel $BP_{ND}$ map onto the secondary scan space comprises co-registration.

In another embodiment, processing the probability-corrected time-activity curve data of the individuals in the control and reference groups to generate voxel mean cortical binding potential ($BP_{ND}$) map data for each individual comprises Logan graphical analysis. In one embodiment, gray matter probability corrected time activity curve of the cerebellum is used as a reference region for the Logan graphical analysis.

In still a further embodiment, the method further comprises a step of processing the secondary space voxel $BP_{ND}$ map data by partial volume correction analysis following the step of transforming the secondary space voxel $BP_{ND}$ map data of the individuals in the control and reference groups onto a standardized space to generate normalized voxel $BP_{ND}$ map data for the individual.

In one embodiment, the partial volume correction analysis comprises a three-compartment method. In another embodiment, the partial volume correction analysis comprises a two-compartment method.

In yet another embodiment, the transforming the secondary space voxel $BP_{ND}$ map data of the individuals in the control and reference groups onto a standardized space to generate normalized voxel $BP_{ND}$ map data for the individual is performed using an algorithm selected from the group consisting of any of Statistical Parametric Mapping (SPM), Simple Affine (AFF) methodology, the Fifth Order Polynomial Warp (WRP) methodology, and the Full Multi Grid (FMG) methodology.

In another embodiment, the transforming the secondary space voxel $BP_{ND}$ map data of the individuals in the control and reference groups onto a standardized space to generate normalized voxel $BP_{ND}$ map data for the individual is performed using an algorithm is selected from the group consisting of AIR, ANIMAL, ART, Diffeomorphic Demons, FNIRT, IRTK, JRD-fluid, ROMEO, SICLE, SyN and FLIRT.

In yet another embodiment, individuals in the control group and the reference group are separated into groups according to the presence or absence of a neurological disorder.

In one embodiment, the neurological disorder is Alzheimer's disease.

In still another embodiment, the computer-implemented method for diagnosing or determining risk of a neurological disorder in a subject further comprises a step of administering the radioligand to the one or more individuals in the control group and to the one or more individuals in the reference group before the step of generating primary brain scan image data of radioligand distribution in a brain of at least one individual in a control group and at least one individual in a reference group.

In yet another embodiment, the radioligand is N-methyl-[$^{11}$C]2-(4-methylaminophenyl)-6-hydroxybenzothiazole.

In still a further embodiment, the primary brain space image data is generated using Positron Emission Tomography.

In yet another embodiment, the secondary brain space image data is generated using Magnetic Resonance Imaging.

BRIEF DESCRIPTION OF THE FIGURES

FIG. 4 shows a workflow for calculating VOI binding, and diagnosing a subject, using data derived VOI and a novel subjects' MRI and methyl-$^{11}$C-2-(4-methylaminophenyl)-6-hydroxybenzothiazole (also known as $^{11}$C-6-OH-BTA-1 or [$^{11}$C]PIB) PET scan.

As shown in FIG. 7, the method can segregate patients that respond to selective serotonin reuptake inhibitors (non-remitters) from patients whose symptoms come back sometime after treatment with serotonin reuptake inhibitors (remitters).

DETAILED DESCRIPTION

Figure 1:
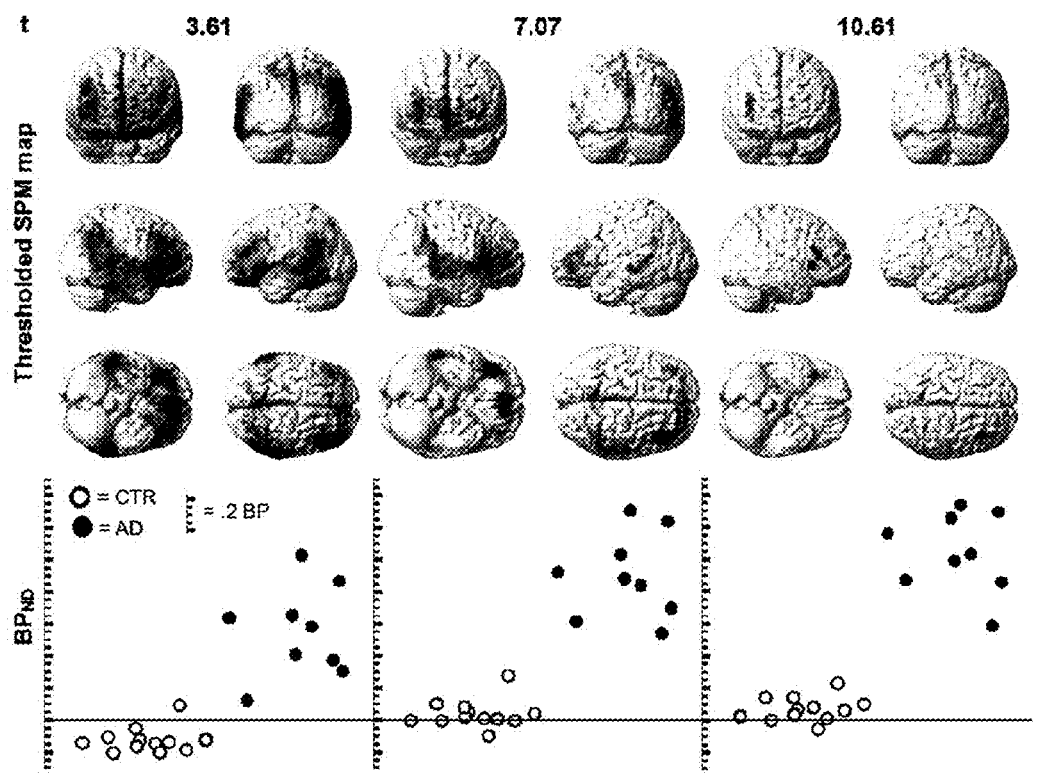
FIG. 1 shows maximum-intensity projections of statistical parametric mapping (SPM) results comparing control and AD subjects for several t-score (t) values.

The issued patents, applications, and other publications that are cited herein are hereby incorporated by reference to the same extent as if each was specifically and individually indicated to be incorporated by reference.

The subject matter disclosed herein relates to a method for diagnosing a neurological disorder (e.g. Alzheimer's disease) in a subject, the method comprising (a) determining one or more critical areas in the brain (e.g. volumes of interest) from PET data where two groups differ and (b) measuring PET signal within determined critical areas in a new subject in order to assign risk or diagnosis.

Definitions

As used herein, the term "brain image data" refers to a representation of brain structure or activity. Examples include, but are not limited to, brain scanning technologies such as MRI, and PET scanning, and other available methods of measuring and recording brain structure or activity.

As used herein a "neurological disorder" is a disorder comprising neurological and/or psychiatric features. Examples include diseases that affect the brain or the mind, including, but not limited to Alzheimer's disease, Parkinson's disease, Mild Cognitive Impairment, depression, pain, psychosis, epilepsy, dementia, migraine, schizophrenia and other psychotic disorders, bipolar disorder, mood disorders such as major or clinical depression, anxiety disorders such as generalized anxiety disorder, somatoform disorders (Briquet's disorder), factitious disorders such as Munchausen syndrome, dissociative disorders such as dissociative identity disorder, sexual disorders such as dyspareunia and gender identity disorder, eating disorders such as anorexia nervosa, sleep disorders such as insomnia and narcolepsy, impulse control disorders such as kleptomania, adjustment disorders, personality disorders such as narcissistic personality disorder, tardive dyskinesia, tourettes, autism, and others, and those described in: Adams & Victor's Principles Of Neurology by Maurice Victor, Allan H. Ropper, Raymond D. Adams.

In one aspect the determination of critical brain areas and the determination of the determining whether a subject has, or at risk of having a neurological disorder can involve the collection of MRI and PET images one or more subjects from two groups of subjects (e.g. a group comprising individuals having a neurological disorder and a reference group comprising individuals not having a neurological disorder).

In one embodiment, the PET scan can be performed using a radioligand. In another embodiment, the PET signal can be from a specific radioligand such as one that binds to molecules found in altered amounts in Alzheimer's Disease. In another embodiment, the PET signal can be from a specific radioligand useful for measuring brain blood flow or metabolism.

In another aspect, the subject matter disclosed herein relates to the use of empirical or data-based derivation of standardized VOIs from [$^{11}$C]PIB scans (or from any radioligand described herein) to improve the sensitivity and specificity of healthy control and AD discrimination. In one embodiment, the VOIs can be derived from partial volume corrected data to increase the signal/noise of VOIs, Standardized VOIs have the additional advantage of being consistent and not susceptible to rater availability, training and variability. The methods described herein can be used to establish a simple, quick way of discriminating between control and AD patients and to develop screening methods using [$^{11}$C]PIB data (or data from any radioligand described herein) for clinical and research purposes.

In still a further aspect, the subject matter disclosed herein relates to the derivation and use of a standardized VOI that functions as a robust metric for Alzheimer's diagnosis based on [$^{11}$C]PIB data. In still a further aspect, the subject matter disclosed herein relates to the derivation and use of a standardized VOI that functions as a robust metric for segregating patients that respond to medication (non-remitters) from those whose symptoms come back (remitters) in a population of patients having Major Depressive Disorder based on [$^{11}$C]WAY-100635 data. In still a further aspect, the subject matter disclosed herein relates to the derivation and use of a standardized VOI that functions as a robust metric for differentiating, segregating, categorizing or diagnosing one or more subjects based on data derived from the use of any radioligand described herein in conjunction with the methods described herein.

In one embodiment, the VOI is automatic and can be used to reduce human error. In another embodiment, an arterial input function can be used to increase the signal and separation of the method. In yet another embodiment, a modeling scheme that does not have a noise dependent bias can be used to further increase signal. In still a further embodiment, analysis can be automated by replacing manual identification of regions of the cerebellum with a template version. Accordingly, the methods described herein provide an automated basis for making the distinction between Alzheimer's and healthy control subjects using [$^{11}$C]PIB. Such a robust metric can improve diagnosis or can be used to select patients with confirmed amyloid deposition for clinical trials involving novel drugs aimed at reducing amyloid load in AD. This method can also be used in patients having a mild cognitive impairment and can be important to assess its ability in predicting conversion to Alzheimer's disease.

Positron Emission Tomography (PET) Using the [$^{11}$C]PIB Radioligand

In one aspect, the subject matter disclosed herein relates to the use of data-determined standardized voxels of interest (VOI) to improve the classification capability of [$^{11}$C]PIB scans in Alzheimer's patients. The uptake pattern and the amount of Aβ present in the brain can be visualized with positron emission tomography (PET) using the PET radioligand N-methyl-[$^{11}$C]2-(4-methylaminophenyl)-6-hydroxybenzothiazole (also known as [11C]6-OH-BTA-1 and [$^{11}$C]PIB). [$^{11}$C]PIB binds to amyloid beta (Aβ) which accumulates pathologically in Alzheimer's Disease (AD). N-methyl-$^3$H}2-[4'-(methylamino)phenyl]6-hydroxybenzothiazole ([$^3$H]PIB) is also suitable for use as an amyloid imaging agent for use with the methods described herein.

Other agents suitable for detecting amyloid deposits include, but are not limited to BF compounds described in U.S. Patent Publication Application No. 2006/0018825 A1, sterylbenzoxazole derivative compound, $^{18}$F-radiolabeled 6-(2-fluoroethoxy)-2-[2-(4-methylaminophenyl)ethenyl]-benzoxazole (BF-168) (Okamura et al. J. Neurosci. 2004, 24 (10), 2535), F-18 labeled 2-(2-[2-diethylaminothiazol-5-yl]-ethenyl)-6-(2-[fluoro])ethoxybenzoxazol (eB F-227) (Kudo et al. J. Nucl. Med. 2007, 48553). Several amyloid deposit imaging compounds suitable for use with the methods described herein include those described U.S. Pat. Nos. 6,001,331; 6,696,039; 6,168,776 and 6,133,259.

[$^{11}$C]PIB accumulation is greater in AD than healthy controls (control) at a group level, however, Aβ formation does not adhere to the boundaries of traditional anatomical regions (3). For this reason, VOIs that have commonly been analyzed (prefrontal, temporal, precuneus, and striatum) might not be optimal regions for diagnosis. There can be overlap between the groups in the frontal/pre-frontal cortex (4, 7) and in other regions (4, 6, 7). This overlap can arise from several measurement parameters including, incorrect clinical diagnosis of AD (2), control samples from subject having incipient AD, unknown ligand specificity (8), partial volume effects (9, 10), inappropriate quantification model (8, 11) or the variability and specificity of the anatomical voxels of interests (VOIs) that have been used to delineate and quantify Aβ binding.

Alternative approaches include total cortical Aβ binding (5, 12) or visual assessment by a radiologist (12). The cortical binding measure does elicit differences between the groups. Studies that reported this measure differed in their outcomes. In one study (5), total group separation was observed, though the distance between the highest control and lowest AD subject were separate by only 0.02 binding potential units. In the other studies (6, 12), several control and AD patients overlapped in their mean cortical binding. Visual diagnosis based on a [$^{11}$C]PIB scan, performed by two trained raters, showed 100% sensitivity and varied (80-88%) in specificity. While this strategy can be effective in ensuring that true AD patients are diagnosed, it can be prone to positive rates and can rely on the availability of trained radiologists, wherein the level or training can result in inter-rated and intrarater variability. This is evident in the study, where the less experienced radiologist scored 8% lower in specificity than the more experienced one. In one aspect, the methods described herein relate to a methods related to automated methods for assessing Aβ accumulation as a diagnostic measure for susceptibility and progression of AD.

In one aspect, the subject matter disclosed herein relates to finding that [$^{11}$C]PIB BP$_{ND}$ images can be used to create a standardized data-derived or empirical set of voxels of interest that be used to confirm clinical diagnosis without the need to define conventional anatomical structures on an individual patient's PET scan. In one embodiment, a standardized template can be created by performing group analysis on a first cohort of control and AD subjects in statistical parametric mapping (SPM) to produce a t-map showing significant (uncorrected, p<1e-4) difference in a contiguous cortical area that spanning conventional anatomical regions.

Thresholded t-map as a VOI

In one aspect, the methods described herein can be used to derive a cortical VOI that is optimized between sampling location and volume. SPM results from control and AD group analysis have shown significant areas of difference (7, 12, 24), however SPM maps alone do not aid in diagnosing or classifying an individual subject but rather describing the group effect. On the region of interest (ROI) level, the prefrontal cortex, caudate and precuneus gyms have shown the greatest discrimination between control and AD patients. For any one anatomical ROI, overlap between groups has been reported (4-7, 12) and ROI, in and of itself, does not ideally separate control and AD groups (6, 12). Accordingly, the success of the cortical binding metric is ultimately dependent on the regions selected.

In another aspect, the methods described herein relate to methods useful for establishing an ideal diagnostic anatomical VOI. In one embodiment, the methods described herein can be used to derive a cortical VOI has been derived empirically to maximize the separation between groups. Unlike previously reported mean-cortical metrics this VOI avoids rater variability, availability and time. The methods described herein can also be used with a single subject's MRI and PET scan and the result can be made available within hours. An exemplary application of this technique to an individual subject is provided herein (e.g. FIG. 4).

In one embodiment, a standardized template VOI optimized can be used for control/AD group discrimination and to provide separation of control and AD subjects based on [$^{11}$C]PIB uptake. This VOI template can serve as a replacement for manual VOI delineation and can be completely automated, facilitating potential use in a clinical setting.

In another embodiment, a standardized template VOI optimized can be used to discriminate and to provide separation of subjects based on [$^{11}$C]WAY-100635 uptake.

In another aspect, the subject matter disclosed herein relates to a method for diagnosing a neurological disorder (e.g. Alzheimer's disease) in a subject, the method may include generating a voxel-based, fully or semi quantitative PET image (this PET image can be generated using an arterial input function or as a ratio of uptake in the voxels to a reference region).

In certain embodiments, the voxel image can be transformed into a subject's MRI-space by performing a PET to MRI alignment (i.e., a "co-registration"). In another embodiment, the voxel image can be transformed into a standard or normalized space (for example, a standard MRI brain space, such as MNI). In certain embodiments, the MRI image can be segmented by statistical parametric mapping (e.g., using SPM5 software). For example, such segmenting can be performed to generate a gray matter image map, a white matter image map or a cerebrospinal fluid (CSF) matter image map. Partial volume correction can be applied to the voxel image using MRI segmented data and this data can be transformed onto a standard space template. A Student's t-test (or equivalent statistical test, such as an ANCOVA) can then be performed for voxels between standard space voxel images of control and reference groups to create a t-score map. In certain embodiments, the groups can be selected such that one group comprises individuals having, or at risk of having a neurological disorder, and the other group corresponds to reference group not having a neurological disorder. The groups can be also selected such that one group consists of individuals having, or at risk of having a neurological disorder, and the other group consists of individuals not having a neurological disorder.

In one aspect, the methods described herein can be performed with a simple template model, whereby all subject data are normalized to a single template in order to establish a common coordinate system to do all subsequent analysis. The single template need not be MNI or Tailarach or any common template or coordinate system. In one embodiment, the template can be in a novel coordinate system created from brain scans of a single subject, average of many subjects, and neurological disorder specific (average of many patient scans). In another embodiment, the template can be based on MRI, PET, or other modality scans (fMRI, DTI, brain acitivity, etc.).

In another aspect, the single template model can be expanded into a multi-template model, whereby different templates for the control and reference groups that have been placed into a common coordinate system. Such can be the case if there are large morphological differences in the control and reference groups.

In one embodiment, the multi-template model can involve registering (linearly or non-linearly) N number of templates to a subject space, instead of a subject to a template space. In this manner, a threshold criteria can be derived from statistical (SPM, ANOVA, t-test) analysis in each subject's space, in their native resolution and scan quality.

Accordingly, the methods describe herein allow for several single or multi-subject template analysis to be combined (either in subject or template space) from separate group analysis such as; control vs reference 1, control vs reference 2, etc.

The t-score maps described herein can contain a t-value for voxels representing the likelihood that the two groups have different ligand binding in that voxel. A plurality of t-score thresholds can then be selected (for example 20 or more t-score thresholds) depending on the t-score range within the t-score map. Selection of these t-score thresholds can be used to determine critical brain areas. The t-score map can then be inverse-transformed into a subject's MRI space data. A group of binary mask images, wherein each binary mask image is created from a different t-score threshold can be then generated. In one embodiment, each binary mask image can be generated by making voxels less than the t-score threshold at each threshold equal to zero and making values greater or equal to the threshold equal to 1. In another embodiment, each binary mask image can be generated by making voxels less than or equal to the t-score threshold at each threshold equal to zero and making values greater to the threshold equal to 1. The binary masks can then be multiplied by the subject's gray matter mask to create a gray matter voxels of interest (VOI) mask for t-score thresholds.

The average gray matter voxel intensity can be calculated by multiplying the native voxel image by the VOI mask and then summing the result and dividing it by the sum of the VOI mask. In certain embodiments, a t-test can be performed between the gray matter voxel intensity of the control and reference groups for t-score thresholds. In one embodiment, VIO can be selected be determining the t-test that produces the lowest p-value.

In certain embodiments, steps between (and including) the generation of the voxel based quantitative PET image and the transformation of the partial volume corrected voxel image onto a standard space template can be repeated for each subject in the control and the reference groups. In certain embodiments, the steps between (and including) the Student's t-test and the calculation of the average gray matter voxel intensity can be repeated for each subject in the control and the reference groups to generate gray matter BP values for each subject at each t-score threshold.

The subject matter disclosed herein also provides methods for optimizing volumes of interest from MRI or PET scans of the brain of a subject, wherein the volumes of interest can be used to determine if the subject has, or is at risk of having a neurodegenerative disease or disorder, for example Alzheimer's disease. In one embodiment, the subject matter disclosed herein provides a method for application of critical brain areas as VOI for diagnosing whether an subject has, or it at risk of having a neurological disorder, wherein the method comprises (a) mapping subject data with a T1 MRI scan, (b) performing a PET scan using the same ligand that was used to create the VOI, (c) using a reference region of interest (ROI) (ligand dependent) manually drawn on MRI or a blood input function with plasma ligand and metabolite fractions, (d) generating a voxel based fully or semi quantitative PET image, (e) transforming the voxel image onto a subject's MRI using parameters from a PET to MRI alignment (co-registration), (f) segmenting the MRI image (if obtained) using SPM5 into gray, white and CSF matter image maps, (g) applying partial volume correction (optional) to the voxel image using MRI segmented data, (h) transforming the VOI from the template space into the subject's native MRI space using inverse transformation parameters from an MRI to Montreal Neurological Institute (MNI) non-linear registration, (i) multiplying the VOI by the subject's gray matter mask to create a gray matter VOI mask, (j) calculating the average gray matter voxel intensity by multiplying the native space voxel image by the gray matter VOI mask, summing the resulting image, and then dividing it by the sum of the gray matter VOI mask.

In one embodiment, the method involves generating a voxel map of the brain of a subject, wherein the method comprises determining the determining the probability that a voxel area is different between the brain of a subject having a neurodegenerative disease or disorder and a normal control subject.

In another embodiment, the map can be shrunk by establishing a threshold of volumes of interest to a template brain and applying the template as a mask to a subject having or at risk of having a neurodegenerative disorder to determine whether the subject has a neurodegenerative disorder.

As described herein, in one embodiment, a standardized template VOI that is optimized for control/AD group discrimination provides separation of control and AD subjects based on [$^{11}$C]PIB uptake.

This VOI template can serve as a replacement for manual VOI delineation and can be fully automated, facilitating potential use in a clinical setting. In one embodiment, the VOI template and software for processing can be made available through the internet for analysis and validation.

One skilled in the art will appreciate that any radioligand described herein can be used in conjunction with the methods of the disclosed subject matter to generate VOI templates to discriminate between any number of individuals or cohorts in a population so long as the radioligand, when used in conjunction with the methods described herein, can be used to generate differential VOIs from scans (e.g. brain scans) of the subjects.

Exemplary radioligands suitable for use with the methods described herein include, but are not limited to, [$^{11}$C]-DTBZ, $^{11}$CFE-CIT, [$^{18}$F]-dopa, [$^{11}$C]-dopa, [$^{18}$F]-CFT, [$^{11}$C]-RTI-32, [$^{18}$F]-FP-CIT, [$^{11}$C]-methylphenidate, [$^{123}$I]-β-CIT, [$^{123}$I]-FP-CIT, [$^{123}$I]-altropane, [$^{99m}$Tc]-TRODAT-1, [$^{11}$C]-dihydrotetrabenazine, [$^{99m}$Tc]-MHMPAO, [$^{99m}$Tc]-ethylcystein dimer, [$^{99m}$Tc]-DTPA, [$^{99m}$Tc]-glucoheptonate, [$^{99m}$Tc]-sestamibi, [$^{99m}$Tc]-tetrofosmin, [$^{99m}$Tc]-labelled sulphur colloid, $H_2^{15}O$, [$^{18}$F]-fluorodeoxyglucose, [$^{13}$N]-ammonium, [$^{15}$O]-butanol, $^{113}$Xe, $^{15}O2$, [$^{11}$C]-CFT, [$^{123}$I]-IPT, [$^{11}$C]-SCH23390, [$^{11}$C]-raclopride, [$^{11}$C]-FLB456, [$^{11}$C]-methylspiperone, [$^{18}$F]-spiperone, [$^{18}$F]-fluroethylspiperone, [$^{76}$Br]-bromospiperone, [$^{123}$I]-epidepride, [$^{123}$I]-iodobenzamide, [$^{11}$C]-BATA, [$^{18}$F]-2-fluorothoxydazoxan, [$^{11}$C]-methyltryptophan, [$^{11}$C]-DASB, [$^{11}$C]-WAY100635, [$^{11}$C]-MDL100907, [$^{18}$F]-altanserin, [$^{18}$F]-serpeptone, [$^{11}$C]-MP4A, [$^{11}$C]-physostigmine, [$^{11}$C]-vesamicol, [$^{123}$I]-benzovesamicol, [$^{11}$C]-tropanylbenylate, [$^{11}$C]-NMPB, [$^{18}$F]-FP-TZTP, [$^{123}$I]-QNB, [$^{11}$C]-MPA, [$^{11}$C]-A-85380, [$^{18}$F]-A-85380, [$^{123}$I]-A-85380, [$^{11}$C]-dothiepin, [$^{11}$C]-carfentenil, [$^{18}$F]-cyclofoxy, [$^{11}$C]-diprenorphine, [$^{11}$C]-flumazenil, [$^{11}$C]-RO15-4513, [$^{11}$C]-PK11195, [$^{18}$F]-PK11195, [$^{123}$I]-PK11195, [$^{18}$F]-SPARQ, [$^{11}$C]-GR205171, [$^{11}$C]-SCH 442416, [$^{11}$C]-CNS 5161, [$^{18}$F]-FDDNP, [$^{11}$C]-SB13, [$^{123}$I]-IMPY, and [$^{11}$C]-carfentenil.

The methods described herein can be used to provide an automated basis for making the distinction between any number of cohorts in a population using any radioligand described herein so long as the radioligand, when used in conjunction with the methods described herein, can be used to generate differential VOIs from scans (e.g. brain scans) of the subjects.

In one embodiment, the methods described herein can be used to segregate subjects in a population among cohorts that are responsive and non-responsive to a particular compound administered to the subject. For example, the methods described herein can also be used to provide an automated basis for making the distinction between non-remitters and remitters of a compound in a population of patients having any neurological disorder (e.g. Major Depressive Disorder) using any radioligand described herein (e.g. [11C]WAY-100635).

Exemplary compounds suitable for use with the methods described herein include, but are not limited to, analgesics, anesthetics (general, local), anorectics, anti-adhd agents, antiaddictives, anticonvulsants, antidementia agents, antidepressants, antimigraine agents, antiparkinson's agents, antipsychotics, anxiolytics, depressants, entactogens, entheogens, euphoriants, hallucinogens (psychedelics, dissociatives, deliriants), hypnotics/sedatives, mood stabilizers, neuroprotectives, nootropics, neurotoxins, orexigenics, serenics, stimulants, and wakefulness-promoting agents.

Examples of antidepressants suitable for use with the methods described herein include, but are not limited to, selective serotonin reuptake inhibitors (SSRIs), serotonin-norepinephrine reuptake inhibitors (SNRIs), noradrenergic and specific serotonergic antidepressants (NaSSAs), norepinephrine (noradrenaline) reuptake inhibitors (NRIs), norepinephrine-dopamine reuptake inhibitors (NDRIs), selective serotonin reuptake enhancers (SSREs), norepinephrine-dopamine disinhibitors (NDDIs), tricyclic antidepressants (TCAs), and monoamine oxidase inhibitor (MAOIs).

Selective serotonin reuptake inhibitors (SSRIs) suitable for use with the methods described herein include, but are not limited to, alaproclate, citalopram, escitalopram, femoxetine, fluoxetine, fluvoxamine, indalpine, ifoxetine, litoxetine, lubazodone, panuramine, paroxetine, pirandamine, seproxetine, sertraline, vilazodone, and zimelidine.

As used herein, the term "neurological disorders" includes, but is not limited to, mild cognitive impairment, Dementia, Alzheimer's disease, multi-infarct dementia, Pick's disease, Creutzfeldt-Jakob disease, Huntington's disease, Parkinson's disease, AIDS dementia complex, frontotemporal dementia, sundowning, wandering, delirium, post-concussion syndrome, organic brain syndrome, intoxication/drug overdose, physical dependence, substance dependence, rebound effect, double rebound, withdrawal, psychosis (e.g. schizoaffective disorder, schizophreniform disorder, brief reactive psychosis), schizophrenia (e.g. disorganized schizophrenia, delusional disorder, folie a deux), mood disorders, mania, bipolar disorders (e.g. bipolar I, bipolar II, cyclothymia, bipolar NOS), depression (e.g. major depressive disorder, dysthymia, seasonal affective disorder, atypical depression, melancholic depression), anxiety disorders, phobias, panic disorder/panic attack, generalized anxiety disorder, OCD, stress disorders (e.g. acute stress reaction, PTSD), adjustment disorder with depressed mood, somatoform disorders, somatization disorder, body dysmorphic disorder, hypochondriasis, nosophobia, Da Costa's syndrome, psychalgia, conversion disorders (e.g. Ganser syndrome, Globus pharyngis), neurasthenia, mass psychogenic illness, dissociative disorders, dissociative identity disorder, psychogenic amnesia, fugue state, depersonalization disorder, eating disorders, anorexia nervosa, bulimia nervosa, rumination syndrome, NOS, nonorganic sleep disorders, nonorganic hypersomnia, nonorganic insomnia, parasomnia disorders (e.g. REM behavior disorder, night terror, nightmare), sexual dysfunction, sexual desire disorders (e.g. hypoactive sexual desire disorder, hypersexuality), sexual arousal (e.g. female sexual arousal disorder), erectile dysfunction, orgasm disorders (e.g. anorgasmia, premature ejaculation), postpartum depression, postnatal psychosis, adult personality and behavior disorders, sexual maturation disorder, ego-dystonic sexual orientation, sexual relationship disorder, paraphilia disorders (e.g. voyeurism, fetishism), personality disorder, impulse control disorder (e.g. kleptomania, Trichotillomania, Pyromania), body-focused repetitive behavior, factitious disorders (e.g. Munchausen syndrome), mental retardation, phychological development disorders, ADHD, conduct disorders (e.g. ODD), emotional disorders (e.g. Separation anxiety disorder), social functioning disorders (e.g. selective mutism, RAD, DAD), tic disorders (e.g. Tourette syndrome), speech disorders (e.g. stuttering, cluttering), movement disorders (e.g. stereotypic movement disorder), catatonia, false pregnancy, intermittent explosive disorder, psychomotor agitation, sexual addiction, stereotypy, psychogenic non-epileptic seizures, Klüver-Bucy syndrome, Emil Kraepelin mood disorder, Karl Leonhard mood disorder, John Cade mood disorder, Mogens Schou mood disorder, Frederick K. Goodwin mood disorder, Kay Redfield Jamison mood disorder, hallucination, delusion, emotional dysregulation disorders (e.g. anhedonia, dysphoria, suicidal ideation), sleep disorders (e.g. hypersomnia, insomnia), psychosis, and racing thoughts.

Identifying Brain Image Phenotypes

In certain aspects, the methods described herein relate to generating determining brain image data. A variety of brain scanning/imaging technologies are currently available, widely in use and adaptable to the present invention. These include magnetic resonance imaging (MRI), functional magnetic resonance imaging (fMRI), Positron Emission Tomography (PET) scanning/imaging, electroencephalograph (EEG) imaging, magnetoencephalography (MEG) imaging, and Computerized Axial Tomography (CAT) scanning/imaging. Further details on the general topic of imaging can be found in the literature, e.g., in Beaumont and Graham (1983) Introduction to Neuropsychology. New York: The Guilford Press; Changeux (1985) Neuronal Man: The Biology of Mind New York: Oxford University Press; Malcom (1994) Mind Fields: Reflections on the Science of Mind and Brain. Grand Rapids, Mich.: Baker Books; Lister and Weingartner (1991) Perspectives on Cognitive Neuroscience. New York: Oxford University Press; Mattson and Simon (1996) The Pioneers of NMR and Magnetic Resonance in Medicine. Dean Books Company; Lars-Goran and Markowitsch (1999) Cognitive Neuroscience of Memory. Seattle: Hogrefe & Huber; Norman (1981) Perspectives on Cognitive Science. New Jersey: Ablex Publishing Corporation; Rapp (2001) The Handbook of Cognitive Neuropsychology. Ann Arbor, Mich.: Psychology Press; Purves et al. (2001) Neuroscience, Second Edition Sinauer Associates, Inc. Sunderland, Mass.; and, The Molecular Imaging and Contrast Agent Database (published on line, current through the present date: http://www.ncbi.nlm.nih.gov/books/bookres.fcgi/micad/home.html).

For example, Magnetic Resonance Imaging (MRI) uses magnetic fields and radio waves to produce dimensional images of brain structures. In MRI, a large magnet creates a magnetic field around the head of the patient, through which radio waves are sent. The magnetic field to aligns the nuclear magnetization of hydrogen atoms in water in the body. Radio frequency fields are used to systematically alter the alignment of this magnetization, causing the hydrogen nuclei to produce a rotating magnetic field detectable by the scanner. Positron emission tomography (PET) is a nuclear medicine imaging technique which produces a three-dimensional image or picture of functional processes in the body. The system detects pairs of gamma rays emitted indirectly by a positron-emitting radionuclide (tracer), which is introduced into the body on a biologically active molecule.

In one embodiment, differences in image data can be determined, by normalization on a standard brain atlas. Brain atlases suitable for use with the methods described herein include, but are not limited to the Talairach brain atlas and the Montreal Neurological Institute (MNI) brain atlas.

The Talairach coordinate system of the human brain, which is used to describe the location of brain structures independent from individual differences in the size and overall shape of the brain. The MNI brain atlas is a more modern brain atlas which is alos useful for coordinating one or more brain structures independently of individual differences in brain shape.

Image Quantification and Analysis

Various types of modeling can be used to quantify receptors in the brain using PET data. Because the activity measured in a PET scan represents a combination of specifically-bound, non-specifically bound, and free (unbound) radioligand, such models can be used to account for dynamic binding of radioligand to target over time.

In semi-quantitative approaches, anatomical regions of interest, including a reference region, can be identified with a scan (e.g. a PET scan) and mathematical models can be used to derive possible binding potentials.

Binding potential (BP) is the term used to describer the ratio of receptor density to the equilibrium dissociation constant of a radioligand (See generally, Mintun et al. Ann Neurol. 1984; 15: 217-227; Innis et al., J Cereb Blood Flow Metab. 2007; 27(9): 1533-1539; Slifstein et al., Nucl. Med. Biol. 2001; 28: 595-608; The Turku PET Center Image Analysis Guide available at http://www.turkupetcentre.fi/index.php?option=com_content&view=article&id=24&Itemid=69&lang=en)

For example, where the free fraction of the radioligand in plasma (i.e. the portion that is not protein-bound), termed $f_P$, can be measured, then the optimal outcome measure, $BP_F$, can be estimated. If $f_P$ cannot be measured due to the limitations of the radioligand, or is not measured by choice, then $BP_P$ can be obtained, which requires the assumption that $f_P$ is equivalent across subjects. The total volume of distribution of a radioligand ($V_T$) can be used to calculate binding potentials (e.g. $BP_F$, $BP_P$, $BP_{ND}$, SUV) for selected reference regions. $BP_{ND}$ is the specific-to-nonspecific equilibrium partition coefficient and is termed semi-quantitative, as it assumes that non-specific, or non-displaceable, binding of the radioligand is equivalent between the groups being compared (Innis, et al., J. Cereb. Blood Flow Metab., 2007, 27, 1533). See generally Miller et al., Current Radiopharmaceuticals, 2008, 1, 12-16; Gunn et al., NeuroImage 1997; 6:279-287; Lammertsma and Hume, NeuroImage 1996; 4:153-158; Boellaard et al., J Nucl Med 2004; 45: 1519-1527; Huang, Nucl Med Biol 2000; 27: 643-646; Thie, J Nucl Med 2004; 45: 1431-1434). For a general description of compartment models see Gunn et al., J Cereb Blood Flow Metab. 2001; 21: 635-652; Lammertsma, Eur Neuropsychopharmacol. 2002; 12: 513-516.; Schmidt and Turkheimer, Q J Nucl Med. 2002; 46:70-85; The Turku PET Center Image Analysis Guide available at http://www.turkupetcentre.fi/index.php?option=com_content&view=article&id=24&Itemid=69&lang=en)

Computer Systems

Figure 6:
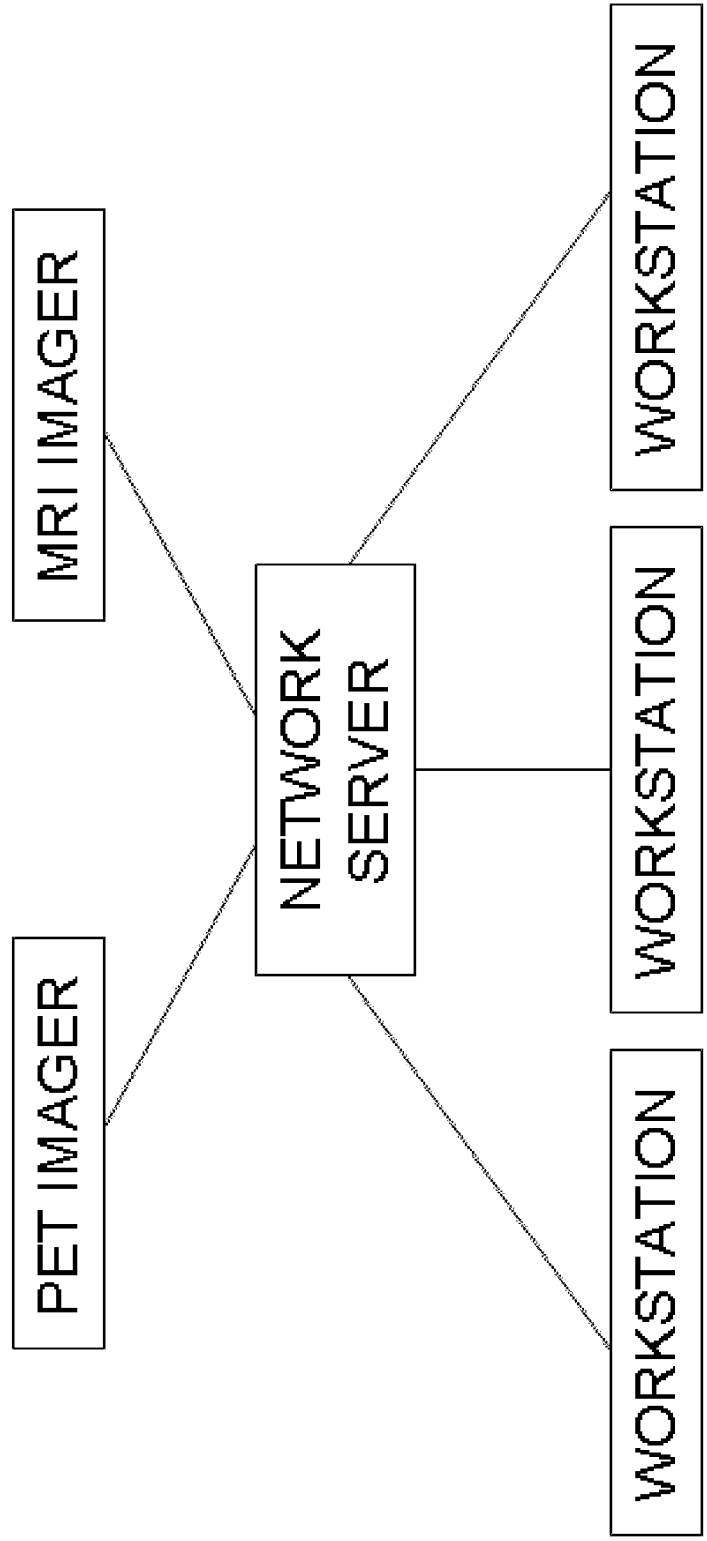
FIG. 6 shows a block diagram of an embodiment of a computer system to implement the methods described herein.

As shown in FIG. 6, the PET and MRI imagers can be connected via a network to a network server (e.g., personal computer, minicomputer, mainframe computer, etc.). Image data can be transferred to the server via the network, or, alternatively, data can be stored on a storage medium by the imaging device and physically transferred to the server, where the data can be read from the storage medium. The server can be connected to one or more workstations (e.g., personal computers, minicomputer workstations, mainframe terminals, etc.) for processing the image data in accordance with the methods described herein. The transfer and processing of the image data can be completely or partially automated depending upon the practicalities of a particular implementation.

One of skill in the art will understand that the methods described herein can be practiced with various types of computer system configurations, including hand-held devices, multiprocessor systems, microprocessor-based or programmable consumer electronics, network PCs, minicomputers, mainframe computers, and the like. The invention can also be practiced in distributed computing environments where tasks are performed by remote processing devices that are linked through a communications network.

In addition, the present invention is not described with reference to any particular programming language. It will be appreciated that a variety of programming languages may be used to implement the teachings of the invention as described herein.

The following examples illustrate the present invention, and are set forth to aid in the understanding of the invention, and should not be construed to limit in any way the scope of the invention as defined in the claims which follow thereafter.

EXAMPLES

Example 1

Comparison of $^{11}$C-PIB $BP_{ND}$ Between Controls and Patients with AD

Empiric or data-based derivation of standardized VIOs from [11C]PIB scans were examined for their ability to improve the sensitivity and specificity of healthy control and AD. VOIs were derived from partial-volume corrected data to increase their signal or noise. Standardized VOIs have the additional advantage of being consistent and not susceptible to rater availability, training, and variability.

The objective of this strategy is to establish a simple, quick, semiautomatic way of discriminating between controls and patients with AD. The results described herein relate to the development of automatic screening methods using [11C]PIB data for clinical and research purposes. To create the standardized VOI set, voxelwise [11C]PIB $BP_{ND}$ partial-volume-corrected cortical gray matter images were derived. The [11C]PIB $BP_{ND}$ partial-volume-corrected cortical gray matter images were generated from a set of controls (n=12) and patients with AD (n=9). Statistical parametric mapping (SPM), extracting the voxels at different statistical significance thresholds and reapplying them to the initial data were used to derive mean cortical binding values. The resulting binding, at different thresholds, was evaluated for group separation and whether some of the overlap found between control and AD groups would be qualified by the use of these new regions, to better support the clinical diagnosis. Finally, the most effective VOI set was tested prospectively in a new cohort of controls (n=4) and patients with AD (n=5).

Sixteen control and fourteen AD age-matched subjects were recruited. All subjects underwent a [11C]PIB scan and had a structural MRI. Binding potential (a measure of amyloid burden) was calculated for voxels using the Logan graphical method with cerebellar gray matter as the reference region.

Voxel maps were then partial-volume corrected and spatially normalized by MRI onto a standardized template. The subjects were divided into 2 cohorts. The first cohort (control, 12; AD, 9) was used for statistical parametric mapping analysis and delineation of data-based VOIs. These VOIs were tested in the second cohort (control, 4; AD, 5) of subjects.

Statistical parametric mapping (SPM) analysis revealed significant differences between control and AD groups. The VOI map determined from the first cohort resulted in complete separation between the control and the AD subjects in the second cohort (P, 0.02). Binding potential values based on this VOI were in the same range as other reported individual and mean cortical VOI results.

The resulting t score map (t=3.61, P, 1E24, uncorrected) from the SPM comparison of the first cohort (control, 12; AD, 9) is shown in FIG. 1 (top). The areas with significant differences are localized to the frontal, parietal, insular, temporal, and precuneus cortices.

Example 2

Creation and Evaluation of Data-Derived VOIs

SPM maps were made into binary masks, using different t score thresholds, and reapplied as VOIs to the control (n=12) and AD (n=9) MRI-$BP_{ND}$-PVC maps of the first cohort. Three representative t maps, thresholded at different t scores, are shown as cortical projections on a rendering of a single subject's T1-weighted MR image (FIG. 1). Dark areas for a given threshold represent the extent of the VOI used to calculate mean cortical binding.

As shown in FIG. 1, the SPM map at each t-score threshold was used to calculate mean subject mean cortical binding potential ($BP_{ND}$) units. Scatter plots of mean cortical $BP_{ND}$ in control and AD groups are shown on the bottom. Maximum-intensity projections of SPM results for several t-score thresholds (top). The SPM map at each t-score threshold created the VOI that was used to calculate mean gray matter $BP_{ND}$ (bottom). There is greater separation between the groups with increasing t threshold. VOIs contain voxels in regions involved in Alzheimer's pathology: prefrontal, parietal, insular, temporal and precuneus cortices. $BP_{ND}$ is calculated for control and AD subjects using the VOI (dark areas) pictured above each scatter plot. Mean cortical $BP_{ND}$ from controls and patients with AD derived from each VOI are shown as scatter plots underneath their corresponding t map (FIG. 1, bottom).

Figures 2A, 2B:
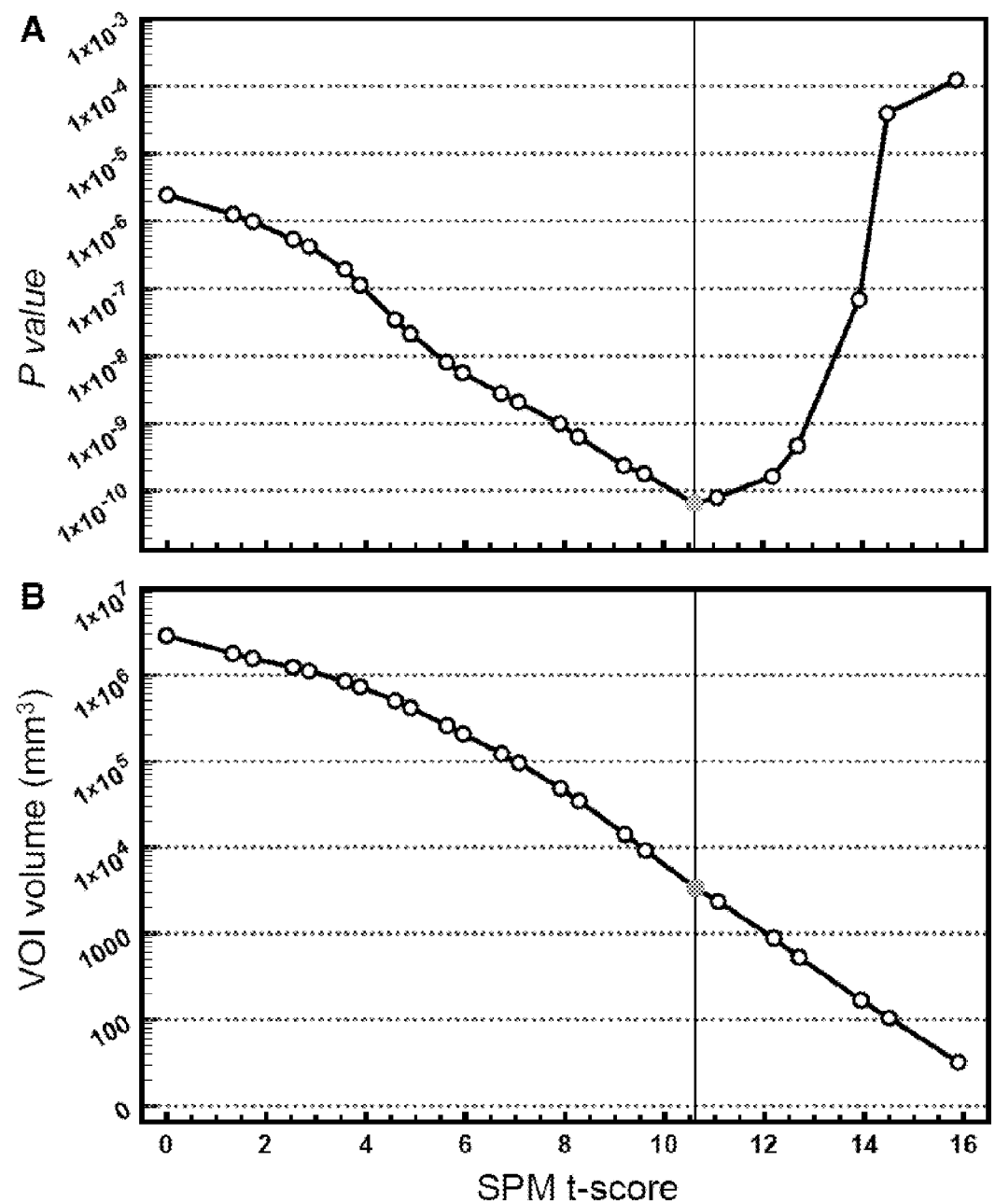
FIG. 2 shows the Effect of SPM map t-score threshold on control vs AD separation (p-value) and VOI volume. Effect of different VOIs, derived by t-score thresholding the SPM map, on CTR/AD separation in terms of p-value (FIG. 2A) and VOI volume (FIG. 2B).

An SPM map was derived from control (n=12) and AD (n=9) partial volume corrected $BP_{ND}$ voxel images. FIG. 2 shows the effect of different VOIs, derived by t-score thresholding the SPM map, on control/AD separation in terms of p-value (FIG. 2A) and VOI volume (FIG. 2B). P values determined by Student t test between the groups at different t score thresholds are shown in FIG. 2A. P-values were calculated by performing a student's t-test on control and AD subjects mean gray matter $BP_{ND}$ for each VOI. The optimal VOI is created using a t-score threshold of 10.61. The map was thresholded at various t-scores and reapplied as VOIs to the MRI space $BP_{ND}$ voxel maps to calculate mean cortical $BP_{ND}$. P values were calculated by performing a students t-test on control and AD groups mean cortical $BP_{ND}$ for t-score thresholds. Group separation increases (decreasing P value) as a function of t score threshold. This increase is evident in the 3 representative scatter plots in FIG. 1. The greatest P value for comparison of the 2 groups occurs at score of 10.61.

The optimal t-score for separation of the groups is 10.61. VOI volume vs t-score is shown in (B). Increasing t-score decreases VOI volume. This trough corresponds to a VOI that is 3,376 mm$^3$ (422 voxels) in MNI space (FIG. 2B). The t-score of 10.61 is represented by a gray circle and horizontal black line. Greatest group separation (smallest p-value) occurs a t-score threshold of 10.61 (vertical line). Up-to a t-score of 10.61, a reduction of VOI size is associated with greater control/AD separation. At this size, the VOI consists of several clusters (excluding clusters with, 10 voxels) of the following location and volume: right frontal lobe (1,632 mm$^3$), left precuneus (608 mm$^3$), right precuneus (184 mm$^3$), right insular cortex (848 mm$^3$), and right temporal lobe (80 mm$^3$) As VOI volume decreases beyond this point, the separation begins to degrade and eventually (FIG. 2B, second to last point, 104 mm$^3$, 13 voxels) is worse than using most of the brain as a VOI (FIG. 2B, first point, 2.8E6 mm$^3$, 3.6E5 voxels).

Example 3

Validation of Data Derived Voxels of Interest in a Second Cohort

The t-map that contained most of the brain when thresholding at a t-score of 1.37 (p<0.01, uncorrected) showed almost complete separation between control and AD, with slight overlap. By empirically testing t-score thresholds, the "best" t-score of 10.61 (p<1e-9, uncorrected) was determined to results in complete and greatest separation between control and AD. Applying this "best" t-score thresholded t-map as a binary VOI to a second cohort of subjects resulted in complete group separation (p<0.02), displaying 100% specificity and sensitivity.

After determination of the best t-score based VOI map for separating the groups (t=10.61), it was applied to the subjects to calculate VOI mean cortical $BP_{ND}$ values. Scatter plots of this data obtained from the subjects MRI-$BP_{ND}$-PVC images for the first cohort and second cohort are shown in FIG. 3.

FIG. 3 shows mean cortical $BP_{ND}$ within VOI derived from SPM t map thresholded at t score of 10.61 (from FIG. 2). VOI was reapplied to first cohort of controls (n=12) and patients with AD (n=9) (A) and applied to second cohort of controls (n=4) and patients with AD (n=5) (B). CTR=control. Comparing control and AD groups from the second cohort resulted in complete separation of the two groups (p<0.02) representing 100% sensitivity and specificity.

The workflow for calculating VOI binding, and diagnosing a subject, using data derived VOI and a novel subjects' MRI and N-methyl-[$^{11}$C]2-(4-methylaminophenyl)-6-hydroxybenzothiazole (also known as [11C]6-OH-BTA-1 and [$^{11}$C] PIB).

Figures 4A, 4B, 4C, 4D:
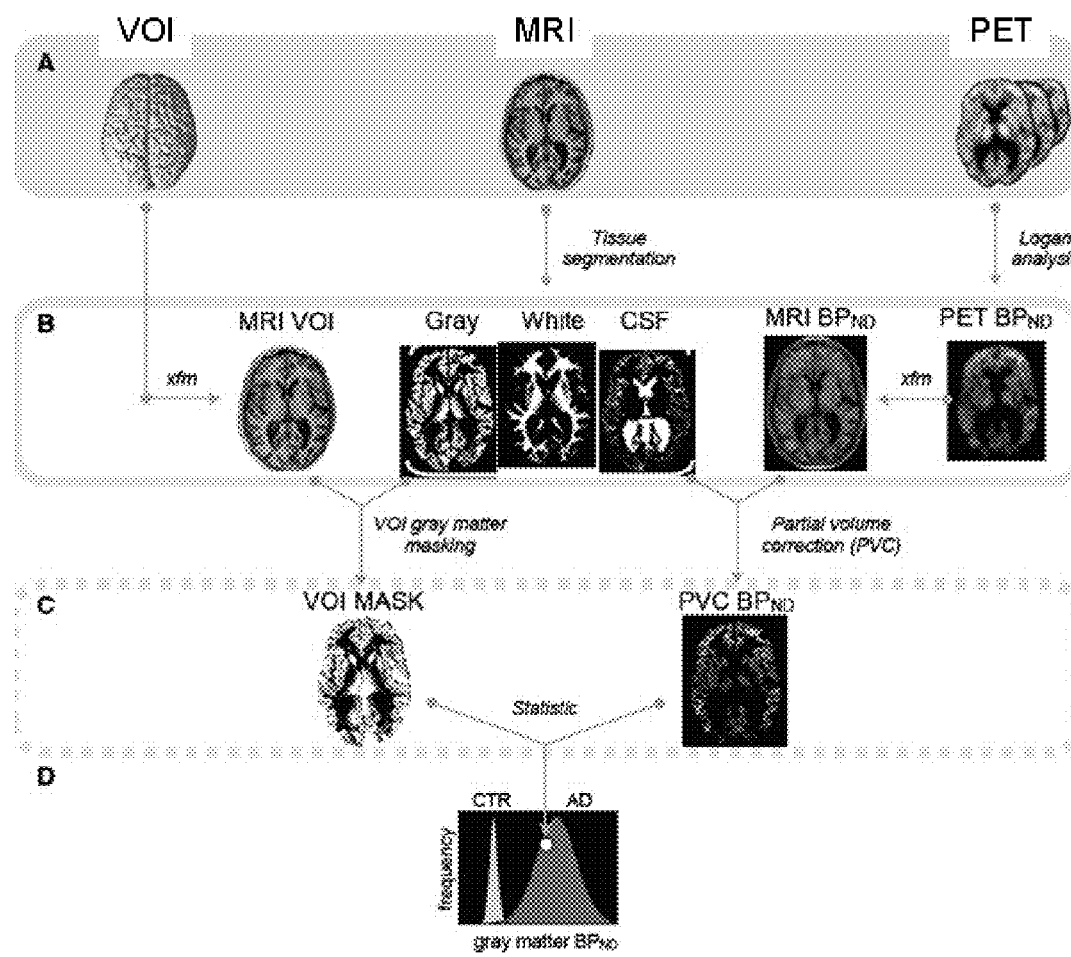
FIG. 4A shows data derived VOI with a subjects' MRI and [11C]PIB PET scan.
FIG. 4B shows The inverse transformation of the VOI into MRI space using parameters from an MRI to MNI normalization.
FIG. 4C shows inverse transformation of the $BP_{ND}$ map into MRI space using parameters from a PET to MRI co-registration.
FIG. 4D shows the final cortical $BP_{ND}$ measure.
Figure 5A:
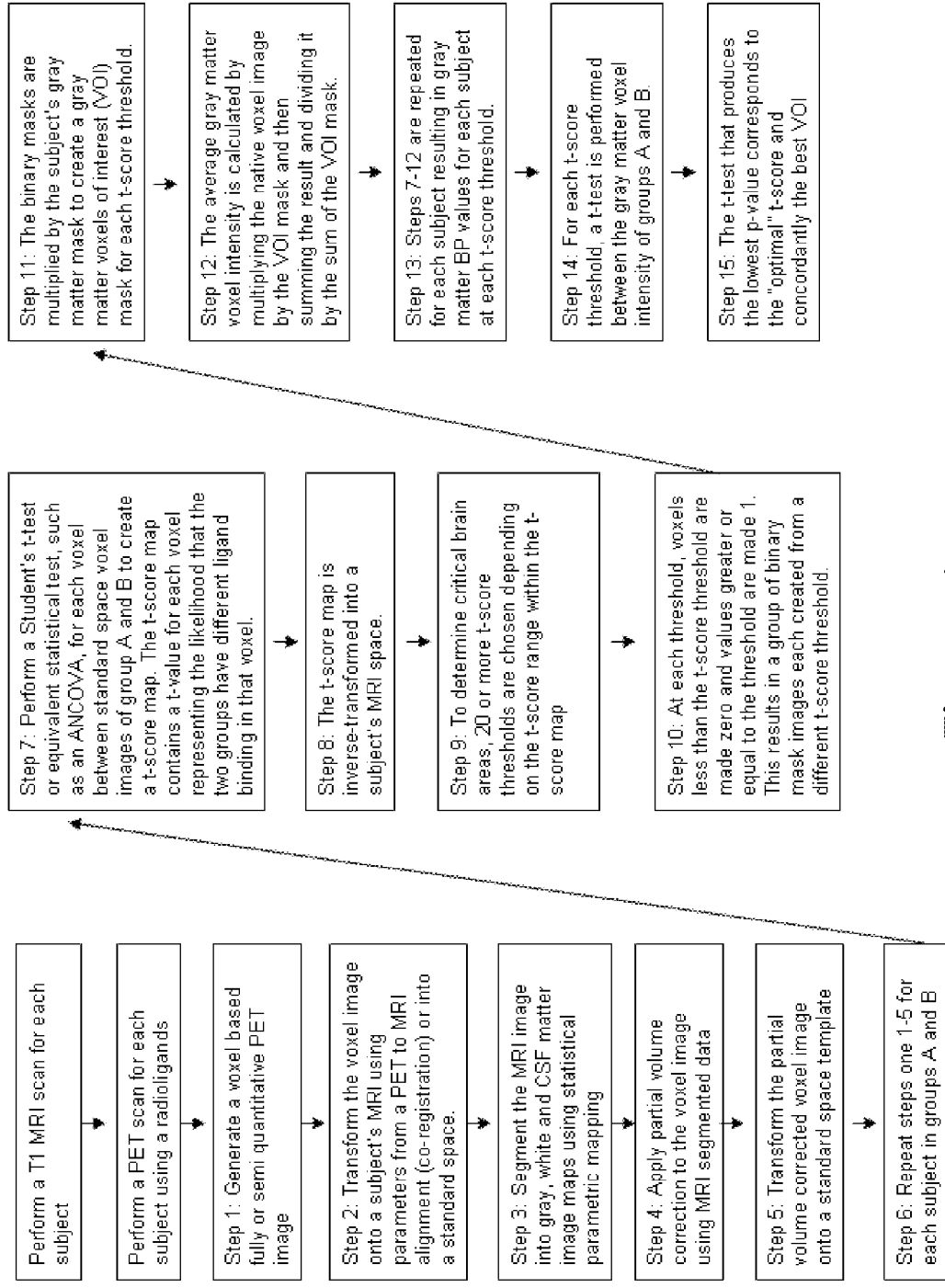
FIG. 5 shows one embodiment of a method for determining (FIG. 5A) and applying critical brain areas (FIG. 5B) a VOI.
Figure 5B:
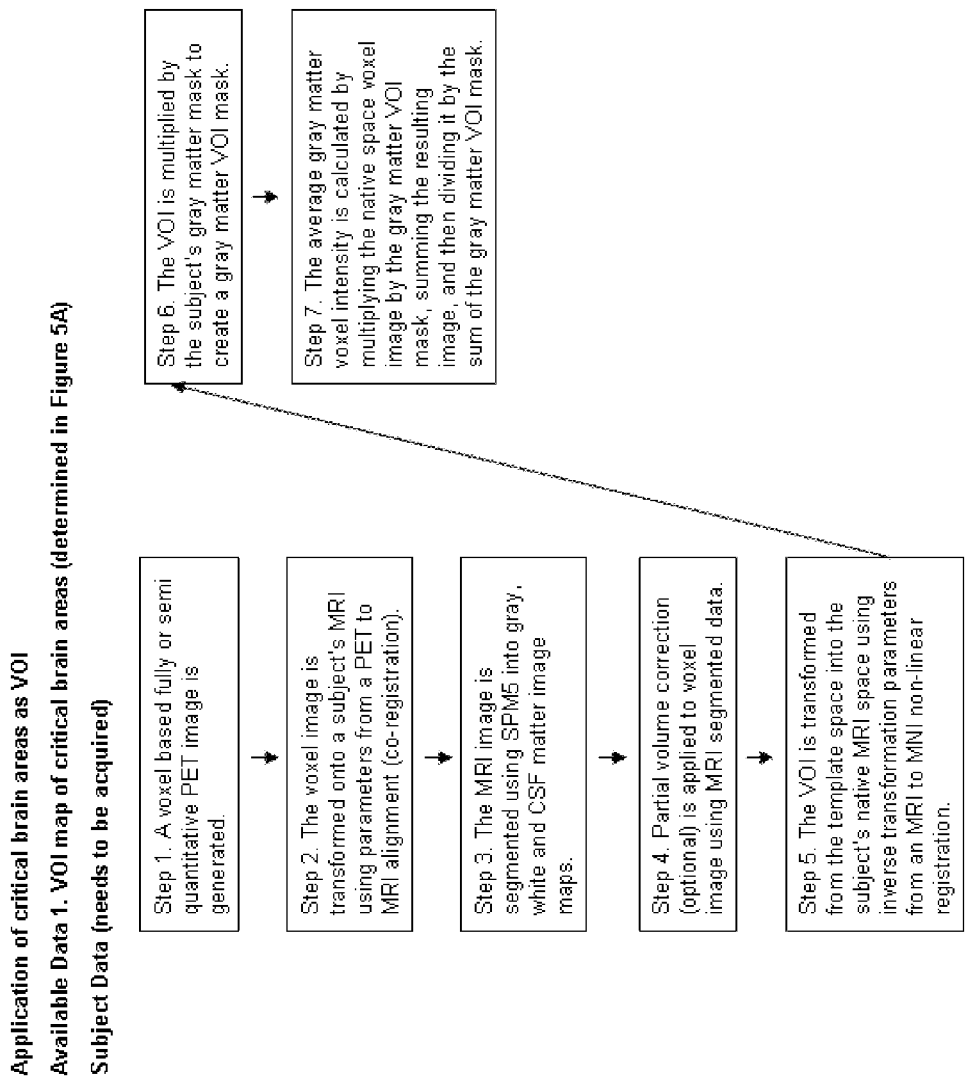

PET scan is shown in FIG. 4. Workflow for calculating mean gray matter binding ($BP_{ND}$), and diagnosing a subject, data derived VOI with a subjects' MRI and [$^{11}$C]PIB PET scan is shown in FIG. 4A. In FIG. 4B the VOI is inverse transformed (xfm) into MRI space using parameters from an MRI to MNI normalization. The MRI is then segmented into gray, white and cerebrospinal fluid (CSF) images. PET data is modeled with the Logan method to derive the $BP_{ND}$ voxel map. The $BP_{ND}$ map is inverse transformed into MRI space using parameters from a PET to MRI co-registration. In FIG. 4C, the MRI VOI is masked to remove non-gray matter voxels (to include only gray matter voxels). Partial volume correction is applied to the $BP_{ND}$ map. In FIG. 4D, the average $BP_{ND}$ value within gray matter VOI voxels is calculated to extract the final cortical $BP_{ND}$ measure. The result (white dot) can be compared to control and AD group results derived with the same process. A single subjects MRI and [$^{11}$C]PIB PET scan can be used to apply the VOI. The VOI can be used to automatically derive mean gray matter $BP_{ND}$ for a single subject.

Figure 3A:
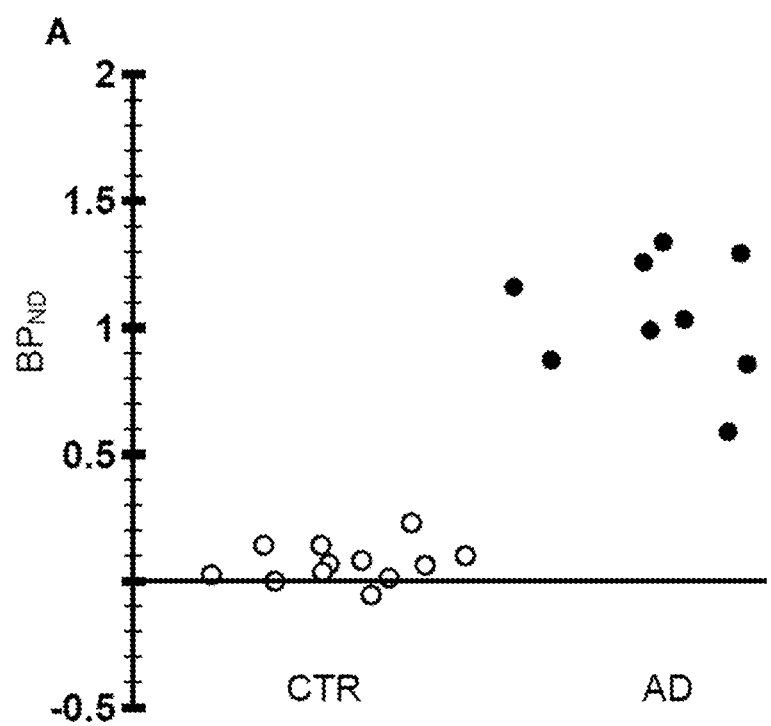
FIG. 3 shows a calculation of mean cortical binding potential ($BP_{ND}$) using data derived VOI thresholded at a t-score of 10.61 (from FIG. 2). The VOI was reapplied to the a cohort of control and AD subjects used to create the VOI (FIG. 3A) and a new cohort of control and AD subjects (FIG. 3B).
Figure 3B:
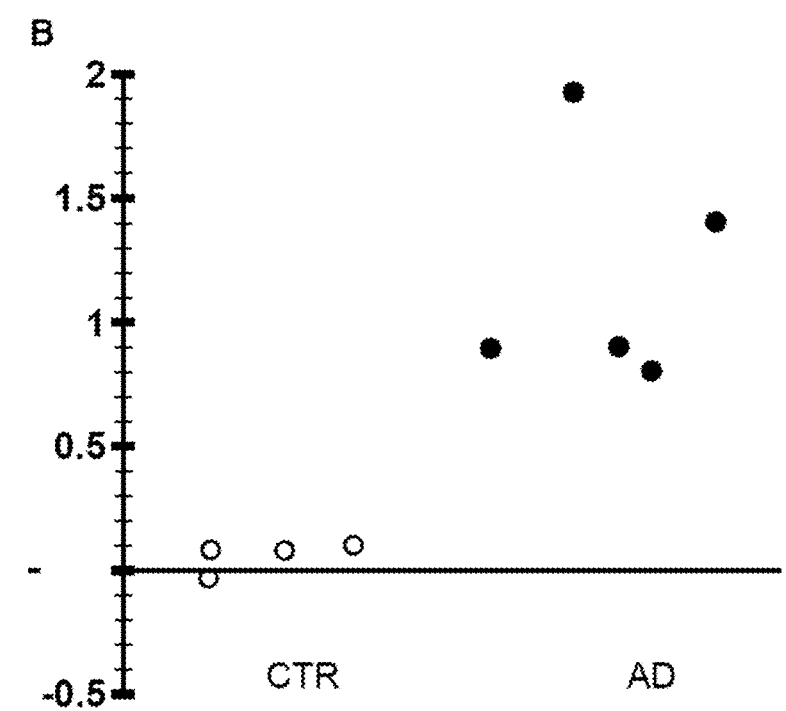

The map is subject to three main sources of variability; location of clusters, volume of the clusters, and laterality. Peak value coordinates within clusters in the VOI (FIG. 3, t=10.61) corresponded to frontal, parietal, insular, temporal and precuneus cortices. Aside from the insular cortex, these regions have been observed to have a high [$^{11}$C]PIB retention in SPM and ROI analysis. The insular cortex has been implicated in both pathology (34) and atrophy (35) of AD patients. Due to the atrophy of this region, partial volume correcting the data can have recovered significant signal in this area. Optimization based on t-score relies on keeping voxels that exhibit larger control/AD separation. This is represented by the decreasing p-value relative to the increasing t-score (FIG. 3A). An inherent consequence of increasing the t-score is decreasing VOI sampling volume (FIG. 3B). Smaller VOI volumes are more specific but also more susceptible to noise. The VOI consists of eleven disjoint clusters (FIG. 1, t=10.61) sampling small areas within larger anatomical structures. Though they are relatively small individually, their combined VOI volume (3372 mm$^3$) is comparable to the average left or right hippocampus volume (~3058 mm$^3$) of the subjects. Template based hippocampus ROIs have been successfully applied to Alzheimer's PET data (36) showing that this volume is sufficient for its use here. Furthermore, the VOI described herein is larger than the hippocampus and is gray matter corrected on an individual basis before calculating mean cortical binding. Gray matter correction has been shown to reduce white matter and CSF noise in small atlas based regions (37).

The VOI exhibits significant right lateralization (FIG. 1, t=10.61). Right lateralization has been reported in [$^{11}$C]PIB SPM voxel analysis using data from 10 AD and 11 control subjects (24). The SPM cohort described herein consisted of a comparable 9 AD and 12 control subjects. The results described herein indicate that right lateralization is not necessarily concomitant with pathology but rather a result of small subject data set. To explicate this, a 3-fold cross validation was performed by generating new SPM maps from randomly selected groups of eight control and eight AD patients. Maps were examined at their optimal t-score threshold. The 3 maps had total VOI volumes of 496 mm$^3$, 1328 mm$^3$, and 2808 mm$^3$. Right lateralization was observed in two of the validation samples but not the third, indicating this is related to the relatively small sample size. When tested on SPM naïve data, all of the maps resulted in nonoverlapping control and AD mean cortical binding. Larger samples can be used to create optimized VOI. Data for a more extensive cross-validation analysis is currently being gathered to qualify voxels included, as well as to test how the VOI is affected with the addition of more subjects.

VOI Partial Volume Correction

To qualify the use of partial volume correction, the SPM VOI was applied to the second cohort of subjects corrected and non-corrected $BP_{ND}$ voxel images. The separation between control and AD groups based on the student's t-test was 0.0045 for the corrected in contrast to 0.0065 for the non-corrected case. The larger separation (smaller p-value) for the partial volume corrected data shows that correction can be applied. Several studies have shown AD or near AD levels of [$^{11}$C]PIB retention in PIB-positive/older controls (4-6, 23), and mild cognitive impaired (5, 11, 23, 38) patients. Partial volume correction can be explored in large sample sizes that include such patients to see if their classification is improved.

The results described herein demonstrate the use of partial volume correcting voxel images before using them for diagnostic purposes aids in classification. Additional control, AD and mild cognitive impaired patient data are being collected to further analyze the effectiveness of partial volume correction.

SPM Analysis

Previously reported group voxel analysis has demonstrated that whether using standardized uptake values (7) or $BP_{ND}$ (7, 12, 24) as an outcome measure, significance reported in Talairach coordinate space is consistent with convention anatomical ROI findings. Statistical thresholds (p-values) and corrections for multiple comparisons (false discovery rate, family wise error) have also been evaluated (24) and found that significance in areas of interest is retained. Thus, groups have been reporting significance based on uncorrected (12) or corrected (7) p-values. Since p-values/t-scores were primarily used to threshold the SPM map, correction was not required.

Processing, Automation and Future Evaluation

It is important for a classification method not be cumbersome or difficult to operate, especially in a clinical environment. The method described herein is designed to qualify the use of PIB voxel data in control and AD discrimination. Aspects of the design may be modified for use as a clinical or research tool. There are several notable analysis complexities; PET scan duration, processing time, MRI availability and cerebellar delineation. The reproducibility of using 90 minute PET data for quantification has been previously demonstrated (11) and is essential for further VOI validation in longitudinal studies. Simplified methods such as 40-60 minute standardized uptake values or 60 minute Logan method may require further validation against more complex and reliable methods.

Processing time can be another important consideration. Currently, once the MRI and PET have been acquired, total processing time for the methods described herein take 2.5 hours (1.5 hours for manual cerebellar delineation and 1 hour processing on a 3 Ghz Xeon machine). This requirement can be decreased in two ways; automated cerebellar labeling and upgrading hardware. Automated ceberellar labeling protocols have been available for some time (i.e. FreeSurfer, LONI Atlases, SUIT, etc.). Once a suitable method is determined it can be initiated as soon as the subjects MRI is acquired so that it is ready before PET acquisition and reconstruction is complete. Personal computer systems with up to 8 processors are now available, some with individual processors as fast as 3.8 GHz. The software and analytical methods described herein are capable of taking advantage of multiple faster processors that would increase speed now and with future technological hardware advances. Existing automatic ceberellar labeling methods are currently being evaluated. Moreover, a cerebellar ROI from an atlas has been created from 16 control brains. The processing speed of the software is also being improved. Furthermore, the cerebellar ROI and the software will be freely available online at: http://brainimagers.info/home/projects/alzheimers in order to facilitate independent analysis and validation. This software can also be used in conjunction with data from the Alzheimer's Disease Neuroimaging Initiative (ADNI) database.

Example 4

Subjects

Sixteen control and fourteen AD patients were recruited for this study. Participants signed informed consent in this IRB-approved protocol. Patients presented with memory complaints to a Memory Disorders Clinic jointly run by the departments of Psychiatry and Neurology at New York State Psychiatric Institute/Columbia University. AD samples were recruited from this pool of patients. AD patients met National Institute of Neurological and Communicative Diseases and Stroke/Alzheimer's Disease and Related Disorders Association (NINCDS-ADRDA) criteria for probable AD (13). Healthy controls were recruited primarily by advertisement, required to have normative mini-mental state exam and selective reminding test scores and meet other patient inclusion/exclusion criteria, and group-matched to patients on age and sex. Subjects were divided into two control and AD cohorts, cohort one and cohort two. Cohort one (12 control, 9 AD) was used for SPM analysis and VOI development while cohort two (4 control, 5 AD) was used for testing and evaluation of the VOI derived from cohort one. Cohort one consisted of subjects available for development at its onset while cohort two consisted of new subjects whose data was acquired consecutively post methods development. Demographic information is shown for cohort one and cohort two in Table 1.

TABLE 1

Demographic data for cohort one, used for initial SPM analysis, and cohort two, used for method evaluation only. Control and AD represent healthy controls and Alzheimer's dementia patients respectively.

|  | Cohort One (SPM) | | Cohort Two (Evaluation) | |
| --- | --- | --- | --- | --- |
| Clinical Diagnosis | Control n = 12 | AD n = 9 | Control n = 4 | AD n = 5 |
| Age | 71.5 ± 8.4 | 65.9 ± 8.5 | 67.8 ± 9.2 | 65.9 ± 8.5 |
| Male/Female | 6/6 | 3/6 | 2/2 | 2/3 |
| MMSE | 28.8 ± .9 | 21.4 ± 3.6 | 21.4 ± 3.6 | 22 ± 1.6 |
| Dose (MBq) | 426 ± 152 | 488 ± 181 | 644 ± 74 | 448 ± 174 |

MMSE is the mini mental state exam score.
Data are means ± standard deviation.

Example 5

[$^{11}$C]PIB Synthesis

The full radiosynthesis of [N-Methyl $^{11}$C]-2-(4-methylaminophenyl)-6-hydroxybenzothiazole ([$^{11}$C]-6-OH-BTA-1) is described elsewhere (14). Briefly, [$^{11}$C]MeOTf was trapped into an acetone (400 microl) solution containing 0.5 mg of 2-(4-aminophenyl)-6-hydroxybenzothiazole at room temperature. The resulting mixture was allowed to react at 60° C. for 2 minutes and allowed to cool to room temperature. The crude product was loaded into a semipreparative HPLC (Phenomenex 18C) column, eluted with 40:60 (acetonitrile: water 0.1 M AMF and 0.5% HOAc, 10 ml/min) and the product fraction was collected between 7 and 8 minutes based on a radiation detector.

The collected fraction was then diluted with deionized water (100 ml), passed through a 18C SepPak, washed with water (10 ml), and the product was eluted from the SepPak with 1 ml of ethanol. A small portion of the product was analyzed with analytical HPLC for chemical and radiochemical purities and specific activity. The remaining ethanol solution was diluted with 9 ml of normal saline, filtered through a 0.22 μm filter and used for further studies. The average yield was found to be 14.5% at EOS with a specific activity >37 GBq/mmol

Example 6

PET Imaging

Subjects' head movement was minimized using a polyurethane head immobilizer molded around the head. PET images were acquired on an ECAT EXACT HR+ (Siemens/CTI, Knoxville Tenn.). Prior to injection a 10-minute transmission scan was acquired. At the end of the transmission scan, between 185 and 740 MBq of [$^{11}$C]PIB was administered intravenously as a bolus over 30 seconds. Emission data were collected in 3D mode for 90 minutes, binning over 18 frames of increasing duration (3×20 sec, 3×1 min, 3×2 min, 2×5 min, and 11×10 min). Images were reconstructed to 128×128 matrix (pixel size of 2.5×2.5 mm$^2$). Reconstruction was performed with attenuation correction using the transmission data and scatter correction was done using a model based approach (15). The reconstruction filter and estimated image filter were Shepp 0.5 (2.5 full width half maximum (FWHM); Siemens/CTI), Z filter was all pass 0.4 (2.0 FWHM; Siemens/CTI), and the zoom factor was 4.0, leading to a final image resolution of 5.1 mm FWHM at the center of the field of view (16).

Example 7

MR Imaging

Magnetic resonance images (MRIs) were acquired using a 1.5 T Signa Advantage system or a 3 T (General Electric Medical Systems, Milwaukee, Wis.). Scans from the 1.5 T camera were acquired in the coronal plane (orthogonal to the anterior commissure posterior commissure plane over the whole brain) with the following parameters; 3D spoiled gradient recalled acquisition in the steady state; TR=34 ms, TE=5 ms, FA=45°, 1.5 mm slice thickness (zero gap), 124 slices, FOV 220 mm×160 mm. Images were reconstructed to a size of 256×256 with a resolution of 1.5×0.86×0.86 mm. Scans from the 3 T camera were acquired with the following parameters; TR=5.4 ms, TE=2.1 ms, FA=11°, 1 mm slice thickness (zero gap), 160 slices, FOV=256 mm×256 mm. Images from the 3 T were reconstructed to a size of 256×256 with an isotropic resolution of 1×1×1 mm.

Example 8

Image Analysis Platform

Image analysis was performed using Matlab 2006b (The Mathworks, MA) with extensions to the following open source packages; Functional Magnetic Resonance Imaging of the Brain's Linear Image Registration Tool (FLIRT) v5.2 (17), Brain Extraction Tool (BET) v1.2 (18), and University College of London's Statistical Parametric Mapping (SPM5) normalization (19) and segmentation routines (20). Other registration tools suitable for use with the methods described herein include, but are not limited to those described in Klein et al, Neuroimage Volume 46, Issue 3, 1 Jul. 2009, Pages 786-802.

Example 9

PET Image Processing

To correct for subject motion during the PET scan, denoising filter techniques were applied to PET images starting at frame five. Frame 8 was used as a reference to which other frames were aligned using rigid body FLIRT. The effectiveness of motion corrected was assessed by viewing a combined movie of pre- and post-motion correction in the sagittal, axial and coronal view. Motion was evaluated for drift between frames and across the entire scan duration separately. For registration, a mean of the motion corrected frames eight through eighteen was registered, using FLIRT, to the subject's BET skull stripped MRI. The resultant transform was applied to the entire motion corrected PET data set to bring the images into MRI space. A mean of the MRI space PET images was then created. This mean image was overlaid onto the MRI to evaluate coregistration.

Example 10

Derivation of Cerebellar Time Activity Data

A region of interest (ROI) was drawn on the MRI, which included the entire cerebellum (volume=121±14 cc). A binary mask of this ROI was then created. To correct the cerebellar ROI to include gray matter only unprocessed MRI images were segmented using SPM5 to derive the probabilistic gray matter (GMp) map. The GMp map and individual PET frames were multiplied (masked) by the cerebellar binary mask. On a frame-by frame basis, the sum of voxels in each masked PET image was divided by the sum of voxels in the masked GMp map to derive the gray matter cerebellar time activity curve.

Example 11

PET Modeling $BP_{ND}$ maps were generated using the Logan graphical method (21) from 90-minute PET data. The gray matter probability corrected time activity curve of the cerebellum was used as a reference. The cerebellum has been shown to be nearly devoid of amyloid plaques in post-mortem analysis (22). Furthermore, cerebellar gray matter shows little [$^{11}$C] PIB retention in control and AD (4). The Logan method is stable, has high test-retest reliability (23), and is sensitive to small changes in [$^{11}$C]PIB when compared to quantification using an arterial input function (11). The Logan method is used in deriving $BP_{ND}$ voxel maps (7, 12, 23, 24), despite its well documented noise dependent bias (8, 25, 26).

Example 12

Partial Volume Correction (PVC)

Regions that share a border with lower or higher binding structures are susceptible to partial volume effect (PVE) due to a blurring caused by the low resolution of PET (27). Since gray matter, white matter and CSF have different [$^{11}$C]PIB uptake patterns (4) gray matter borders undergo PVE. Atrophy of a region that increases the amount of neighboring CSF increases the PVE and cortical atrophy in AD is well established (28). Applying partial volume correction (PVC) to AD data has been shown to increase signal from atrophied tissue in FDG (18F-deoxyglucose) (29) and single photon emission computed tomography (9). In one FDG study (29) signal increase after partial volume correction ranged from 16 to 38% in control and 19 to 49% in AD. Therefore, analyses were performed on PVC [$^{11}$C]PIB binding data. Voxel $BP_{ND}$ maps were transformed onto the MRI space using PET-to-MRI co-registration parameters from above. The maps were then partial volume corrected using a three-compartment method (30). A spherically symmetric point spread function with a FWHM of 5.1 mm was assumed (16), and the white matter mean value was obtained by using the geometric transfer matrix (GTM) method with three compartments (GMp, WMp and CSFp), as previously suggested (10). Three-compartment partial volume correction was utilized as it recovers more gray matter tracer concentration then the two compartment (gray matter, CSF) approach (30, 31). Though it has been suggested that the three-compartment approach is more susceptible to co-registration and motion correction errors (31), the improved methodological and evaluation techniques were utilized to minimize this effect.

Example 13

PET Normalization

The individual's unprocessed MRI was normalized using SPM5 to the ICBM 152 subject 8 mm smoothed T1 template (32, 33). Using the resulting transform parameters MRI space PVC $BP_{ND}$ maps (MRI-$BP_{ND}$-PVC) were shadow transformed onto the individuals MNI normalized MRI (MNI-$BP_{ND}$-PVC).

Example 14

Methods: SPM Analysis

Analysis was executed using the first cohort of subjects control (n=12) and AD (n=9) in SPM5 using their MNI-$BP_{ND}$-PVC images. Prior to analysis images were smoothed using a 8 mm FWHM Gaussian kernel. A two-sample t-test was then done assuming independence and unequal variance, no covariates or masking. Grand-mean scaling or global normalization was not applied, as $BP_{ND}$ is an absolute measurement. The t map, t-score threshold for p-values ranging from 0.5 to 1.0e-12 was obtained at an extent threshold of 0 voxels.

Example 15

SPM Derived VOI Analysis

The t-score thresholds from the SPM analysis were applied to the SPM t-map voxel image by setting voxels less than a particular threshold to zero. Setting remaining voxels greater than zero to one created binary masks of the t-map image. For each threshold, the corresponding binary mask was inverse transformed into each subject's native MRI space and treated as a VOI mask. Multiplying the VOI mask by each subjects $GM_p$ and MRI-$BP_{ND}$-PVC map created a cortical binding map. The sum of the entire resulting image was divided by the mean of the $GM_p$ to derive a mean cortical binding value for the VOI. This was repeated for each first cohort subject. For each VOI, a student's t-test was performed between $BP_{ND}$ results of first cohort control (n=12) and AD (n=9) groups that were used to create the t-score map. By doing this, t-score threshold and hence VOI gaving the best separation was determined.

Example 16

Evaluation

To test the effectiveness of the best t-map threshold derived VOI mask, created from the above analysis, the mask was applied to MRI-$BP_{ND}$-PVC images of a second cohort of control (n=4) and AD (n=5) subjects.

Example 17

General Scheme for the Diagnosis of AD

The method descried herein can be expanded to other disorders and imaging radioligands. Studying these disorders generally involves acquiring a PET and sometimes an MRI for an individual. The PET is used as a measure of the protein and the MRI is used to identify anatomical structures by manual or processor-driven determination of regions of interest (ROIs). The PET is then spatially aligned to the MRI after which the PET can be used to quantify the levels of a protein in identified anatomical structures. To date, no general protocol has been established for using PET to quantitatively assign risk or diagnosis of a disorder to a given subject. The process of ROI determination is poorly reproducible, often labor intensive, and not practicable or feasible for clinicians. The schema is a data-driven, voxel-based processor method that does not require ROIs.

Protocol

First, determine critical areas in the brain from the PET data where two groups differ. Second, measure PET signal within determined critical areas in a new subject in order to assign risk or diagnosis. The PET signal can be from a specific radioligand, such as one that binds to molecules found in altered amounts in Alzheimer's Disease, or radioligands that measure brain blood flow or metabolism.

Software suitable for use with the methods described herein includes, but is not limited to, Matlab 2006b (or higher) software (can be ported to an open source version, Python), freely available SPM5 software, and freely available FSL software.

Determining Critical Brain Areas

Subject Data 2 groups (A and B) of subjects

T1 MRI scan for each subject (useful for the specific application to Alzheimer's disease and other studies).

PET scan for each subject using a radioligands

Processing

Step 1: A voxel based fully or semi quantitative PET image is generated. This may have been generated using an arterial input function or as a ratio of uptake in each voxel to a reference region. Step 2: The voxel image is transformed onto a subject's MRI using parameters from a PET to MRI alignment (co-registration) or is transformed into a standard space. Step 3. The MRI image (if available) is segmented using SPM5 into gray, white and CSF matter image maps. Step 4. Partial volume correction (optional) is applied to the voxel image using MRI segmented data. Step 5. The partial volume corrected voxel image is transformed onto a standard space template. Step 6. Steps one 1-5 are repeated for each subject in groups A and B. Step 7. A Student's t-test or equivalent statistical test, such as an ANCOVA, is performed for each voxel between standard space voxel images of group A and B to create a t-score map. The t-score map contains a t-value for each voxel representing the likelihood that the two groups have different ligand binding in that voxel. Step 8. To determine critical brain areas, 20 or more t-score thresholds are chosen depending on the t-score range within the t-score map. Step 9. The t-score map is inverse-transformed into a subject's MRI space. Step 10. At each threshold, voxels less than the t-score threshold are made zero and values greater or equal to the threshold are made 1. This results in a group of binary mask images each created from a different t-score threshold. Step 11. The binary masks are multiplied by the subject's gray matter mask to create a gray matter voxels of interest (VOI) mask for each t-score threshold. Step 12. The average gray matter voxel intensity is calculated by multiplying the native voxel image by the VOI mask and then summing the result and dividing it by the sum of the VOI mask. Step 13. Steps 7-12 are repeated for each subject resulting in gray matter BP values for each subject at each t-score threshold. Step 14. For each t-score threshold, a t-test is performed between the gray matter voxel intensity of groups A and B. Step 15. The t-test that produces the lowest p-value corresponds to the "optimal" t-score and concordantly the best VOI.

Application of Critical Brain Areas as VOI

Available Data 1. VOI Map of Critical Brain Areas (Determined Above)

Subject Data (Needs to be Acquired)

Step 1. T1 MRI scan (optional). Step 2. PET scan using the same ligand that was used to create the VOI. Step 3. A reference ROI (ligand dependent) manually drawn on MRI OR a blood input function with plasma ligand and metabolite fractions Processing Step 1. A voxel based fully or semi quantitative PET image is generated. Step 2. The voxel image is transformed onto a subject's MRI using parameters from a PET to MRI alignment (co-registration). Step 3. The MRI image (if obtained) is segmented using SPM5 into gray, white and CSF matter image maps. Step 4. Partial volume correction (optional) is applied to voxel image using MRI segmented data. Step 5. The VOI is transformed from the template space into the subject's native MRI space using inverse transformation parameters from an MRI to MNI non-linear registration. Step 6. The VOI is multiplied by the subject's gray matter mask to create a gray matter VOI mask. Step 7. The average gray matter voxel intensity is calculated by multiplying the native space voxel image by the gray matter VOI mask, summing the resulting image, and then dividing it by the sum of the gray matter VOI mask.

Example 18

The PET radioligand N-methyl-[$^{11}$C]2-(4-methylaminophenyl)-6 hydroxybenzothiazole (also known as [$^{11}$C]6-OH-BTA-1 and [$^{11}$C]PIB), binds to amyloid beta (Aβ) which accumulates pathologically in Alzheimer's Disease (AD) [1].

The optimal method for discriminating between healthy control (control) and AD patients has not been previously established. [$^{11}$C]PIB quantification using an anatomical region of interest (ROI) approach requires manual intervention and is subject to radiologist availability, level of training, as well as inter- and intra-rater variability.

The derivation and use of data determined standardized voxels of interest (VOI) for classifying Alzheimer's patients was assessed using [$^{11}$C]PIB scans.

This VOI allows for automatic calculation of mean gray matter binding potential ($BP_{ND}$) using only a single subjects MRI and [$^{11}$C]PIB PET scan. The standardized VOI and software will be freely available through the Internet to facilitate evaluation, testing and improvement.

Sixteen control and fourteen AD age-matched subjects were recruited and underwent [$^{11}$C]PIB PET scan and a structural MRI (Table 1). $BP_{ND}$ voxel maps were created using the Logan graphical method (Logan J, Fowler J S, Volkow N D, Wang G J, Ding Y S, Alexoff D L. Distribution volume ratios without blood sampling from graphical analysis of PET data. J Cereb Blood Flow Metab. September 1996; 16 (5):834-840) with cerebellar gray matter as the reference region (Klunk W E, Engler H, Nordberg A, et al. Imaging brain amyloid in Alzheimer's disease with Pittsburgh Compound-B. Ann Neurol. March 2004; 55 (3):306-319). Voxel maps were partial volume corrected (Muller-Gartner H W, Links J M, Prince J L, et al. Measurement of radiotracer concentration in brain gray matter using positron emission tomography: MRI-based correction for partial volume effects. J Cereb Blood Flow Metab. July 1992; 12 (4):571-583) and spatially normalized by MRI onto a standardized template via SPM5 (Ashburner J, Friston K J. Nonlinear spatial normalization using basis functions. Hum Brain Mapp. 1999; 7 (4):254-266). A t-score map was generated by a student's t-test between 12 control and 9 AD normalized voxel maps in SPM.

The t-score map was thresholded at various t-scores and each time reapplied as a VOI to each subject's native $BP_{ND}$ voxel map to calculate mean gray matter $BP_{ND}$. The t-score threshold resulting in the VOI that produced the "optimal" separation (p-value) between control and AD groups was determined and tested on a new cohort consisting of 4 control and 5 AD subjects.

An empirical set of voxels of interest were derived, and can be applied to [$^{11}$C]PIB images to confirm clinical Alzheimer's diagnosis without the need to define conventional anatomical structures. The voxels of interest reside in regions involved in Alzheimer's pathology.

An automated process for applying these voxels of interest, requiring only a single subject's MRI and [$^{11}$C]PIB PET scan, has been proposed. The automated process can serve as a potential replacement for manual region of interest delineation, facilitating potential use in a clinical setting.

To facilitate independent analysis and validation with a larger and broader variety of subjects, the template and processing software will be made available freely through the Internet.

A template of the cerebellum created from control subjects in this study can be used to replace manual cerebellar delineation. This template will also be made freely available.

Example 19

Segregation of Remitters and Non-Remitters in a Population

Figure 7:
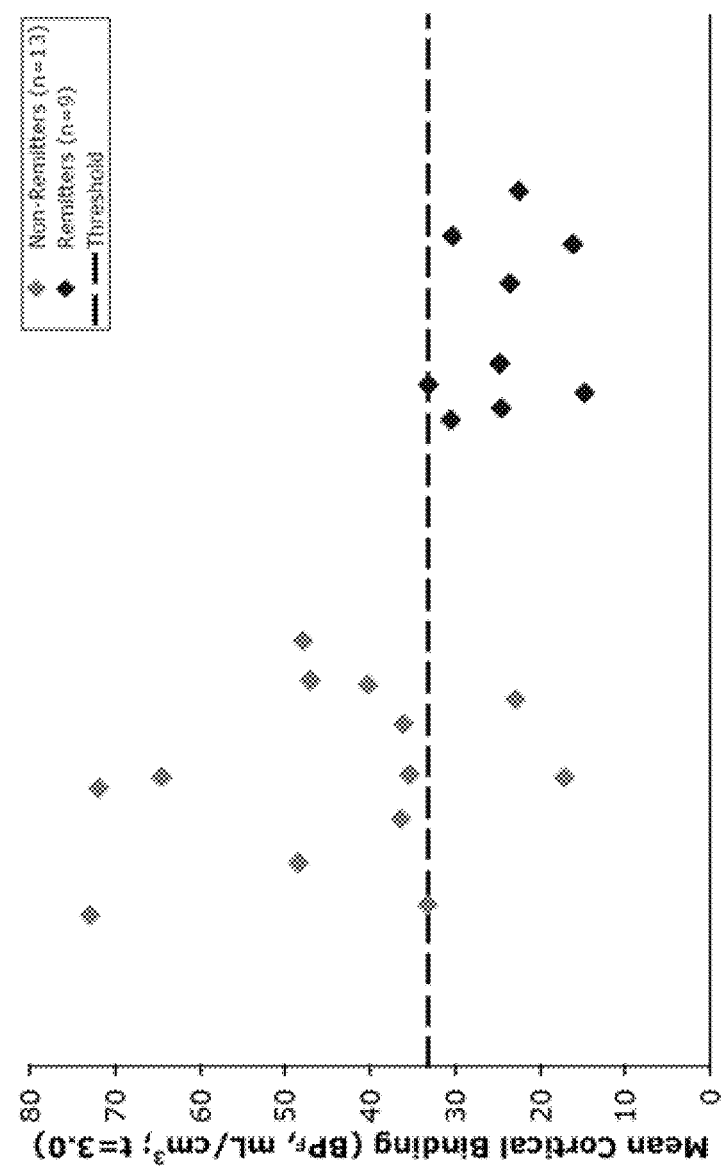
FIG. 7 shows application of the method described herein to measure serotonin receptor levels (as measured by radioligand [$^{11}$C]WAY-100635) in a clinical population having Major Depressive Disorder.
Figure 8:
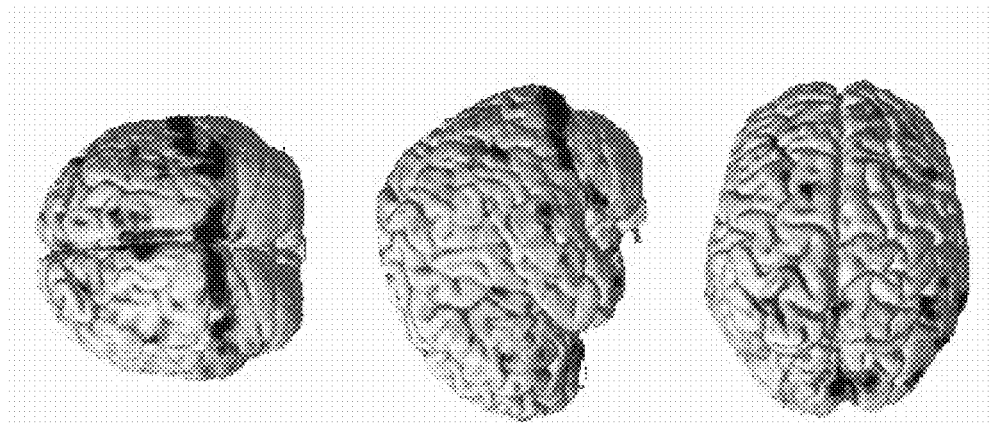
FIG. 8 shows maximum-intensity projections of statistical parametric mapping (SPM) in a three dimensional rendition of the brain. The shaded regions were used to derive the data in FIG. 7. The brain regions shaded in FIG. 8 can be used to segregate between non-remitter and remitter patients in a clinical population having Major Depressive Disorder and are predictive of patient treatment response.
Figure 8:
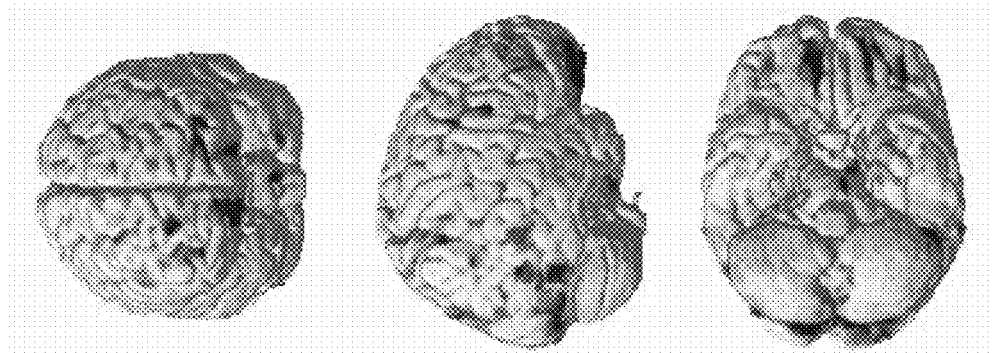
Figure 9:
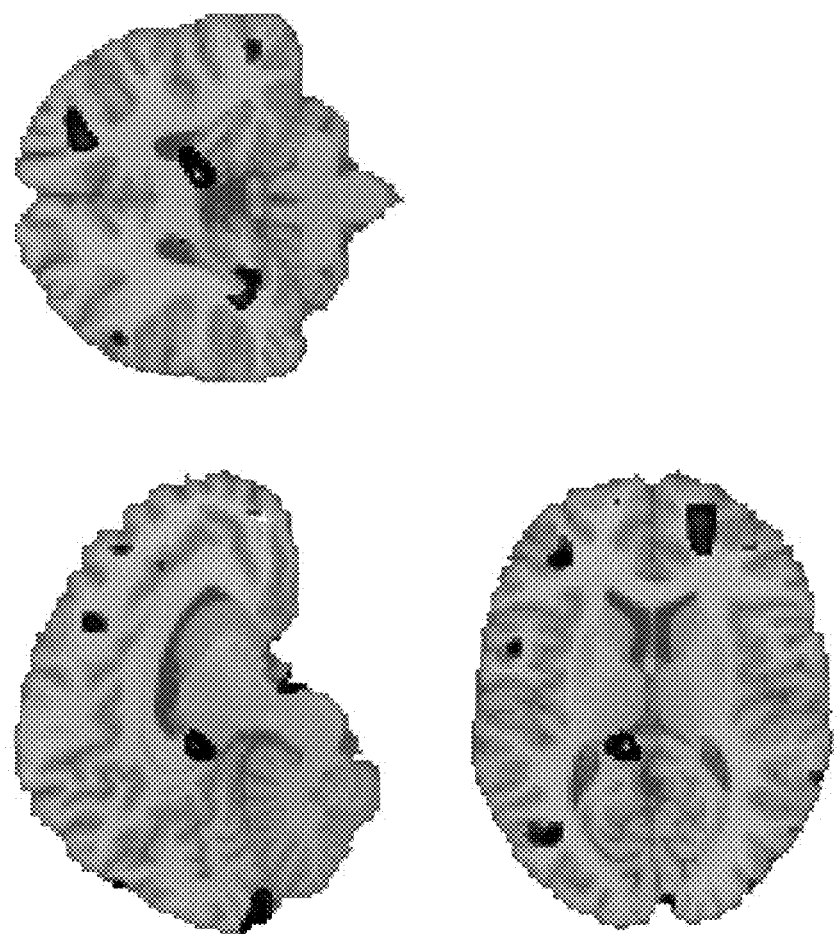
FIG. 9 shows maximum-intensity projections of statistical parametric mapping (SPM) in a cross sectional rendition of the brain. The shaded regions were used to derive the data in FIG. 7. The brain regions shaded in FIG. 9 can be used to segregate between non-remitter and remitter patients in a clinical population having Major Depressive Disorder and are predictive of patient treatment response.

FIGS. 7-9 show the results of applying the methods described herein to a to radioligand (WAY-100635) in a clinical population of subjects having Major Depressive Disorder. FIG. 7 shows that the methods described herein can be used to segregate patients that respond to selective serotonin reuptake inhibitors (non-remitters) from patients whose symptoms come back sometime after treatment with serotonin reuptake inhibitors (remitters). FIGS. 8 and 9, respectively, show a 3D and cross-sectional rendition of the regions of the brain used to derive the data in FIG. 7. The shaded regions shown in FIGS. 8 and 9 were identified as the most sensitive at segregating between non-remitters and remitters in the clinical population of subjects having Major Depressive Disorder. The results described in this example demonstrate that serotonin receptor levels (as measured by WAY-100635) in these specific areas can be predictive of patient treatment response.

REFERENCES

1. Minino A M, Heron M P, Murphy S L, Kochanek K D. Deaths: final data for 2004. *Natl Vital Stat Rep*. Aug. 21 2007; 55 (19):1-119.
2. Zamrini E, De Santi S, Tolar M. Imaging is superior to cognitive testing for early diagnosis of Alzheimer's disease. *Neurobiol Aging*. May-June 2004; 25 (5):685-691.
3. Thal D R, Rub U, Orantes M, Braak H. Phases of A beta-deposition in the human brain and its relevance for the development of AD. *Neurology*. Jun. 25 2002; 58 (12):1791-1800.
4. Klunk W E, Engler H, Nordberg A, et al. Imaging brain amyloid in Alzheimer's disease with Pittsburgh Compound-B. *Ann Neurol*. March 2004; 55 (3):306-319.
5. Rowe C C, Ng S, Ackermann U, et al. Imaging beta-amyloid burden in aging and dementia. *Neurology*. May 15, 2007; 68 (20):1718-1725.
6. Mintun M A, Larossa G N, Sheline Y I, et al. [$^{11}$C]PIB in a nondemented population: potential antecedent marker of Alzheimer disease. *Neurology*. Aug. 8 2006; 67 (3):446-452.
7. Kemppainen N M, Aalto S, Wilson I A, et al. Voxel-based analysis of PET amyloid ligand [$^{11}$C]PIB uptake in Alzheimer disease. *Neurology*. Nov. 14, 2006; 67 (9):1575-1580.
8. Zhou Y, Resnick S M, Ye W, et al. Using a reference tissue model with spatial constraint to quantify [$^{11}$C] Pittsburgh compound B PET for early diagnosis of Alzheimer's disease. *Neuroimage*. June 2007; 36 (2):298-312.
9. Kanetaka H, Matsuda H, Asada T, et al. Effects of partial volume correction on discrimination between very early Alzheimer's dementia and controls using brain perfusion SPECT. *Eur J Nucl Med Mol Imaging*. July 2004; 31 (7): 975-980.
10. Rousset O G, Ma Y, Evans A C. Correction for partial volume effects in PET: principle and validation. *J Nucl Med*. May 1998; 39 (5):904-911.
11. Lopresti B J, Klunk W E, Mathis C A, et al. Simplified quantification of Pittsburgh Compound B amyloid imaging PET studies: a comparative analysis. *J Nucl Med*. December 2005; 46 (12): 1959-1972.
12. Ng S, Villemagne V L, Berlangieri S, et al. Visual assessment versus quantitative assessment of 11C-PIB PET and 18F-FDG PET for detection of Alzheimer's disease. *J Nucl Med*. April 2007; 48 (4):547-552.
13. McKhann G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. *Neurology*. July 1984; 34 (7):939-944.
14. Parsey R V, Sokol L O, Belanger M J, et al. Amyloid plaque imaging agent [C-11]-6-OH-BTA-1: biodistribution and radiation dosimetry in baboon. *Nucl Med Commun*. October 2005; 26 (10):875-880.
15. Watson C C N D, Casey M E. A single scatter simulation technique for scatter correction in 3D PET. *Dordrecht*. 1996.
16. Mawlawi O, Martinez D, Slifstein M, et al. Imaging human mesolimbic dopamine transmission with positron emission tomography: I. Accuracy and precision of D(2) receptor parameter measurements in ventral striatum. *J Cereb Blood Flow Metab*. September 2001; 21 (9):1034-1057.
17. Jenkinson M, Smith S. A global optimisation method for robust affine registration of brain images. *Med Image Anal*. June 2001; 5 (2):143-156.
18. Smith S M. Fast robust automated brain extraction. *Hum Brain Mapp*. November 2002; 17 (3):143-155.
19. Ashburner J, Friston K J. Nonlinear spatial normalization using basis functions. *Hum Brain Mapp*. 1999; 7 (4):254-266.
20. Ashburner J, Friston K J. Unified segmentation. *Neuroimage*. Jul. 1 2005; 26 (3):839-851.
21. Logan J, Fowler J S, Volkow N D, Wang G J, Ding Y S, Alexoff D L. Distribution volume ratios without blood sampling from graphical analysis of PET data. *J Cereb Blood Flow Metab*. September 1996; 16 (5):834-840.
22. Joachim C L, Morris J H, Selkoe D J. Diffuse senile plaques occur commonly in the cerebellum in Alzheimer's disease. *Am J Pathol*. August 1989; 135 (2):309-319.
23. Price J C, Klunk W E, Lopresti B J, et al. Kinetic modeling of amyloid binding in humans using PET imaging and Pittsburgh Compound-B. *J Cereb Blood Flow Metab*. November 2005; 25 (11): 1528-1547.
24. Ziolko S K, Weissfeld L A, Klunk W E, et al. Evaluation of voxel-based methods for the statistical analysis of PIB PET amyloid imaging studies in Alzheimer's disease. *Neuroimage*. Oct. 15 2006; 33 (1):94-102.
25. Logan J, Fowler J S, Volkow N D, Ding Y S, Wang G J, Alexoff D L. A strategy for removing the bias in the graphical analysis method. *J Cereb Blood Flow Metab*. March 2001; 21 (3):307-320.

26. Kimura Y, Naganawa M, Shidahara M, Ikoma Y, Watabe H. PET kinetic analysis—pitfalls and a solution for the Logan plot. *Ann Nucl Med*. January 2007; 21 (1):1-8.
27. Hoffman E J, Huang S C, Phelps M E. Quantitation in positron emission computed tomography: 1. Effect of object size. *J Comput Assist Tomogr*. June 1979; 3 (3):299-308.
28. Chetelat G, Landeau B, Eustache F, et al. Using voxel-based morphometry to map the structural changes associated with rapid conversion in MCI: a longitudinal MRI study. *Neuroimage*. Oct. 1 2005; 27 (4):934-946.
29. Meltzer C C, Zubieta J K, Brandt J, Tune L E, Mayberg H S, Frost J J. Regional hypometabolism in Alzheimer's disease as measured by positron emission tomography after correction for effects of partial volume averaging. *Neurology*. August 1996; 47 (2):454 461.
30. Muller-Gartner H W, Links J M, Prince J L, et al. Measurement of radiotracer concentration in brain gray matter using positron emission tomography: MRI-based correction for partial volume effects. *J Cereb Blood Flow Metab*. July 1992; 12 (4):571-583.
31. Meltzer C C, Kinahan P E, Greer P J, et al. Comparative evaluation of MR-based partial-volume correction schemes for PET. *J Nucl Med*. December 1999; 40 (12): 2053-2065.
32. Mazziotta J C, Toga A W, Evans A, Fox P, Lancaster J. A probabilistic atlas of the human brain: theory and rationale for its development. The International Consortium for Brain Mapping (ICBM). *Neuroimage*. June 1995; 2 (2):89-101.
33. Mazziotta J, Toga A, Evans A, et al. A probabilistic atlas and reference system for the human brain: International Consortium for Brain Mapping (ICBM). *Philos Trans R Soc Lond B Biol Sci*. Aug. 29 2001; 356 (1412):1293-1322.
34. Royall D R, Gao J H, Kellogg D L, Jr. Insular Alzheimer's disease pathology as a cause of "age-related" autonomic dysfunction and mortality in the non-demented elderly. *Med Hypotheses*. 2006; 67 (4):747-758.
35. Foundas A L, Eure K F, Seltzer B. Conventional MRI volumetric measures of parietal and insular cortex in Alzheimer's disease. *Frog Neuropsychopharmacol Biol Psychiatry*. October 1996; 20 (7):1131-1144.
36. Mosconi L, Tsui W H, De Santi S, et al. Reduced hippocampal metabolism in MCI and AD: automated FDG-PET image analysis. *Neurology*. Jun. 14 2005; 64 (11):1860-1867.
37. Rusjan P, Mamo D, Ginovart N, et al. An automated method for the extraction of regional data from PET images. *Psychiatry Res*. Jun. 30 2006; 147 (1):79-89.
38. Kemppainen N M, Aalto S, Wilson I A, et al. PET amyloid ligand [$^{11}$C]PIB uptake is increased in mild cognitive impairment. *Neurology*. May 8, 2007; 68 (19):1603-1606.

What is claimed is:

1. A computer-implemented method for diagnosing or determining risk of a neurological disorder in a subject, the method comprising:
   (a) determining the presence of a radioactive signal from an administered radioligand in at least one individual in a control group and at least one individual in a reference group to generate primary brain scan image voxel data of radioligand distribution in a brain of at least one individual in a control group and at least one individual in a reference group,
   (b) generating secondary brain scan image data for the individuals in the control and reference groups, wherein the secondary scan brain image data is generated using a different type of brain scan than the primary brain scan image data,
   (c) generating a probability-corrected time-activity curve data for each voxel in the primary brain scan image of the at least one individual in the control and reference group,
   (d) processing the probability-corrected time-activity curve data of the at least one individual in the control and reference group to generate a voxel binding outcome map data of the at least one individual in the control and reference group,
   (e) transforming the voxel binding outcome map data of the at least one individual in the control and reference group into a normalized space to generate a normalized voxel binding outcome map data of the at least one individual in the control and reference group
   (f) processing the normalized voxel binding outcome map data of the at least one individual in the control and reference group using statistical analysis to identify one or more voxels of interest (VOI) in the normalized voxel binding outcome map data to generate a VOI map data for differentiating of the at least one individual in the control and reference group, and
   (g) applying the VOI map data to a voxel binding outcome map data of a test subject to generate a mean cortical binding value to diagnose or determine risk of a neurological disorder in the subject wherein the voxel binding outcome map data of said test subject is generated from Positron Emission Tomography (PET) using a PET scanner.

2. The method of claim 1, wherein the transforming of step (e) comprises transforming the voxel binding outcome map data of the at least one individual in the control and reference group into a secondary scan space to generate a secondary space voxel binding outcome map data of the at least one individual in the control and reference group.

3. The method of claim 1, wherein step (g) comprises:
   (i) inverse transforming the VOI map data identified in step (f), into a secondary scan space of the test subject to generate a voxel of interest (VOI) mask for the test subject,
   (ii) multiplying the VOI mask for the subject by probabilistic brain region (BR$_P$) map data for the subject to generate a brain region VOI mask for the subject,
   (iii) multiplying a secondary space voxel binding outcome map data of the subject by the brain region VOI mask for the subject to generate cortical binding map data for the subject, and
   (iv) summing the cortical binding map data of the subject and then dividing it by the sum of the brain region VOI mask to generate a mean cortical binding value.

4. The method of claim 3, wherein the method further comprises a step of processing the secondary brain scan image data of the subject by partial volume correction analysis.

5. The method of claim 1, wherein the generating a probability-corrected time-activity curve data for each voxel in the primary brain scan image of the at least one individual in the control and reference group in step (c) comprises:
   (i) processing the secondary brain scan image data of the at least one individual in the control and reference group to generate a binary brain region mask and probabilistic brain region (BR$_P$) map data for each individual, and
   (ii) processing the probabilistic brain region (BR$_P$) map data and the primary brain scan image data of the at least one individual in the control and reference group onto the binary brain region mask of the individual to generate the a probability-corrected time-activity curve data for each voxel in the primary brain scan image of the at least one individual in the control and reference group.

6. The method of claim 2, wherein the normalized voxel binding outcome map data of the at least one individual in the control and reference group is generated by transformation of secondary space voxel binding outcome map data of the individual into a standard brain atlas.

7. The method of claim 6, wherein the standard brain atlas is a Talairach brain atlas or a Montreal Neurological Institute (MNI) brain atlas.

8. The method of claim 6, wherein the standard brain atlas is a specific brain atlas created for a particular neurological disorder.

9. The method of claim 6, wherein the standard brain atlas is a custom brain atlas.

10. The method of claim 3, wherein the inverse transforming is performed using parameters from an MRI to standard brain atlas registration.

11. The method of claim 1, wherein the processing in step (f) comprises:
  (i) generating a binary voxel image mask of the at least one individual in the control and reference group by statistical parametric mapping analysis,
  (ii) inverse transforming the binary voxel image mask of the at least one individual in the control and reference group into a secondary space voxel binding outcome map data of the individual to generate a voxel of interest (VOI) mask,
  (iii) multiplying the VOI mask of the at least one individual in the control and reference group by the individual's probabilistic brain region ($BR_P$) map data and secondary space voxel binding outcome map data to generate cortical binding map data for the individual,
  (iv) dividing the sum of the cortical binding map of the at least one individual in the control and reference group and the reference group by the mean of the probabilistic brain region ($BR_P$) map data of the individual to generate a mean cortical binding outcome value for the statistical parametric mapping analysis applied in step (i),
  (v) performing statistical analysis between the mean cortical binding outcome values of the at least one individual in the control and reference group to generate a map assigning a probability value to each voxel, and
  (vi) identifying a scoring threshold providing maximal separation of mean cortical binding outcome values between the at least one individual in the control and reference group, wherein the VOI corresponding to the scoring threshold providing maximal separation of mean cortical binding outcome between individuals from the control group and individuals from the reference group is a VOI map data suitable for differentiating individuals in the reference group from individuals in the control group.

12. The method of claim 3 or 11, wherein the secondary space voxel binding outcome map data is generated using a different type of brain scan than the primary brain scan image data used in step (a) of claim 1.

13. The method of claim 11, wherein the statistical analysis in step (v) is a Student's t test.

14. The method of claim 11, wherein the generating of the binary voxel image mask in step (i) comprises applying one or more threshold values to the normalized voxel binding outcome map data such that, for each threshold, data in the voxel binding outcome map data equal to or exceeding the threshold value are retained in the binary voxel image mask and data in the voxel binding outcome map data less than the threshold value are not retained in the binary voxel image mask.

15. The method of claim 14, wherein the one or more threshold values are greater or equal to a value of 50% mean cortical binding outcome in each voxel in the normalized voxel binding outcome map data.

16. The method of claim 14, wherein the one or more threshold values are greater or equal to a value of 90% mean cortical binding outcome in each voxel in the normalized voxel binding outcome map data.

17. The method of claim 14, wherein the one or more threshold values are greater or equal to a value of 99% mean cortical binding outcome in each voxel in the normalized voxel binding outcome map data.

18. The method of claim 1, wherein the primary brain scan image data is generated using an arterial input function as a reference.

19. The method of claim 1, wherein the secondary brain scan image data is from the cerebellum of the individual.

20. The method of claim 1, wherein the secondary brain scan image data is from one or more regions of the cerebellum.

21. The method of claim 1, wherein the secondary brain scan image data is from one or more regions of having reduced radioligand binding.

22. The method of claim 2, wherein the transforming the voxel binding outcome map data of the at least one individual in the control and reference group into a normalized space comprises co-registration.

23. The method of claim 1, wherein the processing in step (c) comprises Logan graphical analysis.

24. The method of claim 23, wherein a brain region probability corrected time activity curve of the cerebellum is used as a reference region.

25. The method of claim 3, 5, 11 or 24, wherein the brain region is gray matter.

26. The method of claim 3, 5, 11 or 24, wherein the brain region is white matter.

27. The method of claim 3, 5, 11 or 24, wherein the brain region is cerebrospinal fluid.

28. The method of claim 3, 5, 11 or 24, wherein the brain region is a brain region comprising one of more voxels in step (c) of claim 1.

29. The method of claim 1, wherein the normalized space voxel binding outcome map data is processed by partial volume correction before step (g).

30. The method of claim 29, wherein the partial volume correction analysis comprises a three-compartment method.

31. The method of claim 29, wherein the partial volume correction analysis comprises a two-compartment method.

32. The method of claim 1, wherein the transforming in step (e) is performed using an algorithm selected from the group consisting of any of Statistical Parametric Mapping (SPM), Simple Affine (AFF) methodology, the Fifth Order Polynomial Warp (WRP) methodology, and the Full Multi Grid (FMG) methodology.

33. The method of claim 1, wherein the transforming in step (e) is performed using an algorithm is selected from the group consisting of AIR, ANIMAL, ART, Diffeomorphic Demons, FNIRT, IRTK, JRD-fluid, ROMEO, SICLE, SyN and FLIRT.

34. The method of claim 1, wherein individuals in the control group and the reference group are separated into groups according to the presence or absence of a neurological disorder.

35. The method of claim 1, wherein the neurological disorder is Alzheimer's disease.

36. The method of claim 1, wherein the neurological disorder is a reduced responsiveness to a compound administered to the subject as compared to a control subject.

37. The method of claim 1, wherein the neurological disorder is an increased responsiveness to a compound administered to the subject as compared to a control subject.

38. The method of claim 36 or 37, wherein the compound is a selective serotonin reuptake inhibitor.

39. The method of claim 1, wherein the neurological disorder is selected from the group consisting of mild cognitive impairment, Dementia, Alzheimer's disease, multi-infarct dementia, Pick's disease, Creutzfeldt-Jakob disease, Huntington's disease, Parkinson's disease, AIDS dementia complex, frontotemporal dementia, sundowning, wandering, delirium, post-concussion syndrome, organic brain syndrome, intoxication/drug overdose, physical dependence, substance dependence, rebound effect, double rebound, withdrawal, psychosis (e.g. schizoaffective disorder, schizophreniform disorder, brief reactive psychosis), schizophrenia (e.g. disorganized schizophrenia, delusional disorder, folie à deux), mood disorders, mania, bipolar disorders (e.g. bipolar I, bipolar II, cyclothymia, bipolar NOS), depression (e.g. major depressive disorder, dysthymia, seasonal affective disorder, atypical depression, melancholic depression), anxiety disorders, phobias, panic disorder/panic attack, generalized anxiety disorder, OCD, stress disorders (e.g. acute stress reaction, PTSD), adjustment disorder with depressed mood, somatoform disorders, somatization disorder, body dysmorphic disorder, hypochondriasis, nosophobia, Da Costa's syndrome, psychalgia, conversion disorders (e.g. Ganser syndrome, Globus pharyngis), neurasthenia, mass psychogenic illness, dissociative disorders, dissociative identity disorder, psychogenic amnesia, fugue state, depersonalization disorder, eating disorders, anorexia nervosa, bulimia nervosa, rumination syndrome, NOS, nonorganic sleep disorders, nonorganic hypersomnia, nonorganic insomnia, parasomnia disorders (e.g. REM behavior disorder, night terror, nightmare), sexual dysfunction, sexual desire disorders (e.g. hypoactive sexual desire disorder, hypersexuality), sexual arousal (e.g. female sexual arousal disorder), erectile dysfunction, orgasm disorders (e.g. anorgasmia, premature ejaculation), postpartum depression, postnatal psychosis, adult personality and behavior disorders, sexual maturation disorder, ego-dystonic sexual orientation, sexual relationship disorder, paraphilia disorders (e.g. voyeurism, fetishism), personality disorder, impulse control disorder (e.g. kleptomania, Trichotillomania, Pyromania), body-focused repetitive behavior, factitious disorders (e.g. Munchausen syndrome), mental retardation, psychological development disorders, ADHD, conduct disorders (e.g. ODD), emotional disorders (e.g. Separation anxiety disorder), social functioning disorders (e.g. selective mutism, RAD, DAD), tic disorders (e.g. Tourette syndrome), speech disorders (e.g. stuttering, cluttering), movement disorders (e.g. stereotypic movement disorder), catatonia, false pregnancy, intermittent explosive disorder, psychomotor agitation, sexual addiction, stereotypy, psychogenic non-epileptic seizures, Klüver-Bucy syndrome, Emil Kraepelin mood disorder, Karl Leonhard mood disorder, John Cade mood disorder, Mogens Schou mood disorder, Frederick K. Goodwin mood disorder, Kay Redfield Jamison mood disorder, hallucination, delusion, emotional dysregulation disorders (e.g. anhedonia, dysphoria, suicidal ideation), sleep disorders (e.g. hypersomnia, insomnia), psychosis, and racing thoughts.

40. The method of claim 36 or 37, wherein the compound is selected from the group consisting of an analgesic, an anesthetic, an anorectic, an anti ADHD agent, an antiaddictive, an anticonvulsant, an antidementia agent, an antidepressant, an antimigraine agent, an antiparkinson's agent, an antipsychotic, an anxiolytic, a depressant, an entactogen, an entheogen, an euphoriant, a hallucinogen, hypnotics/sedative, a mood stabilizer, a neuroprotective, a nootropic, a neurotoxins, an orexigenic, a serenic, a stimulant, and a wakefulness-promoting agent.

41. The method of claim 1, further comprising a step of administering the radioligand to the one or more individuals in the control group and to the one or more individuals in the reference group before step (a).

42. The method of claim 1, wherein the radioligand is N-methyl-[$^{11}$C]2-(4-methylaminophenyl)-6-hydroxybenzothiazole.

43. The method of claim 1, wherein the radioligand is [$^{11}$C]WAY-100635.

44. The method of claim 1, wherein the radioligand is selected from the group consisting of [$^{11}$C]-DTBZ, $^{11}$CFE-CIT, [$^{18}$F]-dopa, [$^{11}$C]-dopa, [$^{18}$F]-CFT, [$^{11}$C]-RTI-32, [$^{18}$F]-FP-CIT, [$^{11}$C]-methylphenidate, [$^{123}$I]-β-CIT, [$^{123}$I]-FP-CIT, [$^{123}$I]-altropane, [$^{99m}$Tc]-TRODAT-1, [$^{11}$C]-dihydrotetrabenazine, [$^{99m}$Tc]-MHMPAO, [$^{99m}$Tc]-ethylcystein dimer, [$^{99m}$Tc]-DTPA, [$^{99m}$Tc]-glucoheptonate, [$^{99m}$Tc]-sestamibi, [$^{99m}$Tc]-tetrofosmin, [$^{99m}$Tc]-labelled sulphur colloid, $H_2^{15}O$, [$^{18}$F]-fluorodeoxyglucose, [$^{13}$N]-ammonium, [$^{15}$O]-butanol, $^{11}$Xe, $^{15}O_2$, [$^{11}$C]-CFT, [$^{123}$I]-IPT, [$^{11}$C]-SCH23390, [$^{11}$C]-raclopride, [$^{11}$C]-FLB456, [$^{11}$C]-methylspiperone, [$^{18}$F]-spiperone, [$^{18}$F]-fluroethylspiperone, [$^{76}$Br]-bromospiperone, [$^{123}$I]-eppidepride, [$^{123}$I]-iodobenzamide, [$^{11}$C]-BATA, [$^{18}$F]-2-fluorothoxydazoxan, [$^{11}$C]-methyltryptophan, [$^{11}$C]-DASB, [$^{11}$C]-MDL100907, [$^{18}$F]-altanserin, [$^{18}$F]-serpeptone, [$^{11}$C]-MP4A, [$^{11}$C]-physostigmine, [$^{18}$F]-fluoroethozybenzoessamicol, [$^{11}$C]-vesamicol, [$^{123}$I]-benzovesamicol, [$^{11}$C]-tropanylbenylate, [$^{11}$C]-NMPB, [$^{18}$F]-FP-TZTP, [$^{123}$I]-QNB, [$^{11}$C]-MPA, [$^{11}$C]-A-85380, [$^{18}$F]-A-85380, [$^{123}$I]-A-85380, [$^{11}$C]-dothiepin, [$^{11}$C]-carfentenil, [$^{18}$F]-cyclofoxy, [$^{11}$C]-diprenorphine, [$^{11}$C]-flumazenil, [$^{11}$C]-R015-4513, [$^{11}$C]-PK11195, [$^{18}$F]-PK11195, [$^{123}$I]-PK11195, [$^{18}$F]-SPARQ, [$^{11}$C]-GR205171, [$^{11}$C]-SCH 442416, [$^{11}$C]-CNS 5161, [$^{18}$F]-FDDNP, [$^{11}$C]-SB13, [$^{123}$I]-IMPY, and [$^{11}$C]-carfentenil.

45. The method of claim 1, wherein the primary brain space image is generated using Positron Emission Tomography.

46. The method of claim 1, wherein the secondary brain space image is generated using Magnetic Resonance Imaging.

47. The method of claim 1, wherein the binding outcome is a specific-to-nonspecific equilibrium partition coefficient ($BP_{ND}$).

48. The method of claim 1, wherein the binding outcome is a binding potential relative to plasma ($BP_P$).

49. The method of claim 1, wherein the binding outcome is a binding potential relative to free plasma concentration ($BP_F$).

50. The method of claim 1, wherein the binding outcome is standardized uptake value (SUV).

51. The method of claim 1, wherein the binding outcome is determined by a standardization technique that generates a qualitative or quantitative measure of radioligand uptake or binding.

* * * * *